United States Patent [19]
Guelcher et al.

[11] Patent Number: 5,910,254
[45] Date of Patent: *Jun. 8, 1999

[54] METHOD FOR DEWATERING MICROALGAE WITH A BUBBLE COLUMN

[75] Inventors: Scott Arthur Guelcher, Weirton, W. Va.; Jeffrey Scott Kanel, Kingsport, Tenn.

[73] Assignee: Eastman Chemical Company, Kingsport, Tenn.

[*] Notice: This patent issued on a continued prosecution application filed under 37 CFR 1.53(d), and is subject to the twenty year patent term provisions of 35 U.S.C. 154(a)(2).
This patent is subject to a terminal disclaimer.

[21] Appl. No.: 08/770,284
[22] Filed: Dec. 20, 1996
[51] Int. Cl.$^6$ ...................................................... B03D 1/02
[52] U.S. Cl. .......................... 210/703; 47/1.4; 209/164; 435/67; 435/946; 514/458; 514/725
[58] Field of Search ................................ 47/1.4; 209/164; 210/703, 634; 435/67, 946; 514/458, 725

[56] References Cited

U.S. PATENT DOCUMENTS

| | | | |
|---|---|---|---|
| 3,268,606 | 8/1966 | Jaeger | 260/666 |
| 3,521,400 | 7/1970 | Ort | 47/1.4 |

(List continued on next page.)

FOREIGN PATENT DOCUMENTS

| | | | |
|---|---|---|---|
| 72394 | 2/1976 | Australia | 47/1.4 |
| 72395 | 2/1976 | Australia | 47/1.4 |
| 0 523 883 | 1/1993 | European Pat. Off. | 47/1.4 |
| 0 586 255 | 3/1994 | European Pat. Off. | 47/1.4 |
| 0 612 725 | 8/1994 | European Pat. Off. | 47/1.4 |
| 2 367 705 | 5/1978 | France | 47/1.4 |
| 1 541 345 | 2/1979 | United Kingdom | 47/1.4 |

OTHER PUBLICATIONS

Rose, P.D. et al.; "Cross–flow Ultrafiltration Used in Algal High Rate Oxidation Pond Treatment of Saline Organic Effluents with the Recovery of Products of Value"; *Water Science and Technology*; 1992; vol. 25, No. 10; pp. 319–327.

Smith, P.H. et al.; "Froth Flotation for Harvesting Chlorella Algae"; *Northwest Science*, vol. 42, No. 4, 1968; pp. 165–171.

(List continued on next page.)

*Primary Examiner*—Ernest G. Therkorn
*Attorney, Agent, or Firm*—Morgan, Lewis & Bockius LLP

[57] ABSTRACT

A process for dewatering an aqueous suspension of microalgae is disclosed in which the aqueous suspension of the algae is introduced into a bubble column or a modified bubble column for generating a froth of bubbles and adsorbed algal cells that can be separated from the aqueous suspension. In one advantageous embodiment, the bubble column is a multi-stage loop-flow flotation column that has three loop-flow zones, each of which is defined by a draft tube concentrically mounted in the column to divide each loop-flow zone into a riser and the downcomer. Fine bubbles of gas and brine are in cocurrent upward flow in the riser and in cocurrent downward flow the downcomer. A higher gas holdup is promoted in the riser than in the downcomer, thereby circulating the brine in loop-flow upwardly through the riser and downwardly through the downcomer. Liquid communication between adjacent loop-flow zones is substantially eliminated. A froth enriched in algae is generated that can be separated from the aqueous suspension. The process has application in the recovery of mixed carotenoids from *Dunaliella salina*.

34 Claims, 10 Drawing Sheets

U.S. PATENT DOCUMENTS

| | | | |
|---|---|---|---|
| 3,645,040 | 2/1972 | Ort | 47/1.4 |
| 4,115,949 | 9/1978 | Avron et al. | 47/1.4 |
| 4,199,895 | 4/1980 | Avron et al. | 47/1.4 |
| 4,253,271 | 3/1981 | Raymond | 47/1.4 |
| 4,341,038 | 7/1982 | Bloch et al. | 47/1.4 |
| 4,439,629 | 3/1984 | Rüegg | 585/803 |
| 4,554,390 | 11/1985 | Curtain et al. | 568/870 |
| 4,680,314 | 7/1987 | Nonomura | 514/725 |
| 4,851,339 | 7/1989 | Hills | 435/67 |
| 4,938,865 | 7/1990 | Jameson | 209/168 |
| 4,958,460 | 9/1990 | Nielson et al. | 47/1.4 |
| 4,981,582 | 1/1991 | Yoon et al. | 209/164 |
| 5,167,798 | 12/1992 | Yoon et al. | 209/170 |
| 5,188,726 | 2/1993 | Jameson | 209/164 |
| 5,310,554 | 5/1994 | Haigh | 424/439 |
| 5,332,100 | 7/1994 | Jameson | 209/164 |
| 5,378,369 | 1/1995 | Rose et al. | 210/637 |

OTHER PUBLICATIONS

Chemical Abstracts 85400C; Vendt, V.P. et al.; "Experimental–industrial Preparation of Carotene from Natural Brine Containing the Algae Dunaliella Salina"; Nov. 18, 1968; vol. 69, No. 21, p. 7972.

D.X. He., et al., "A Multiple–Loop Flotation Column For Wastewater Treatment", *Separations Technology* 5 (1995), pp. 133–138.

N. Sammy, "Pilot β–Carotene Production: The Northern Territory Experience", *Seventh Symposium on Salt* vol. 1, pp. 679–684 (1993).

T.P. Moulton et al., "The Mass Culture of *Dunaliella vividis* (Volvocales, Chlorophyta) for Oxygenated Carotenoids: Laboroatory and Pilot Plant Studies", Hydrobiologia 204/205, pp. 401–408 (1990).

C.C. Curtain et al., "Manufacture of β–Carotene from the Salt Lake Alga *Dunaliella saliana;* the Scientific and Technical Background", *Australian Journal of Biotechnology,* vol. 1, No. 3, pp. 51–57 (1987).

L. J. Borowitzka et al., "Commercial Production of β–Carotene by *Dunaliella salina* in Open Ponds", *Bulletin of Marine Science,* 47(1), pp. 244–252 (1990).

I. Enes et al., "Optimization of Operating Strategies in β–Carotene Microalgae Bioreactors", *Computers Chem. Engng.,* vol. 20 Suppl., pp. S509 (1996).

T.P. Moulton et al., "The Mass Culture of *Dunaliella salina* for β–Carotene: From Pilot Plant to Production Plant", *Hydrobiologia* 151/152, pp. 99–105 (1987).

G. Shelef, "High–Rate Algae Ponds For Wastewater Treatment and Protein Production", *Wat. Soi. Tech.* vol. 14, pp. 439–452 (1982).

L. Schlipalius, "The Extensive Commercial Cultivation of *Dunaliella Salina"*, *Bioresource Technology* 38 pp. 241–243 (1991).

S.S. Honeycutt, "A Technique for Harvesting Unicellular Algae Using Colloidal Gas Aphrons", *Biotechnology and Bioengineering Symp.* No. 13, pp. 567–575 (1983).

METHOD FOR DEWATERING MICROALGAE WITH A BUBBLE COLUMN

FIELD OF THE INVENTION

The invention relates to methods for recovering components from algae. More specifically, the invention relates to methods for recovering mixed carotenoids from *Dunaliella salina*.

BACKGROUND OF THE INVENTION

Carotenoids are deep yellow-orange pigments found in orange and yellow colored vegetables and in many dark green foods. Beta carotene is the most abundant of the various carotenoids. Beta carotene can be converted by the body to vitamin A. Vitamin A is a fat soluble vitamin that can be stored in the body for a limited period of time, primarily in the liver, unlike the water soluble vitamins, which are not storable. Vitamin A can be toxic if ingested in large amounts. However, beta carotene is converted by the body into vitamin A as needed and typically is considered a non-toxic source of vitamin A even in large amounts.

Beta carotene has been identified as an antioxidant that is capable of countering the damaging effects of oxidation in animal tissues. For this reason and as a nontoxic source of vitamin A, beta carotene has been highly valued and commercially important as a nutritional supplement. However, concerns have recently arisen regarding the health benefits of beta carotene as a nutritional supplement isolated from the mixed carotenoids in which beta carotene typically is found in nature.

Plant derived mixed carotenoids, including beta carotene, can be obtained from a number of sources including carrots, spinach, and palm oil, but their relative concentration is higher in algae of the genus Dunaliella. These algae are commonly found in concentrated salt solutions. Under appropriate growth conditions, more than ten percent of the algal dry weight can be mixed carotenoids.

For example, *Dunaliella salina* tends to accumulate significant amounts of carotenoids and glycerol when stressed by exposure to high temperatures, intense light, and brine solutions having a concentration of sodium chloride of greater than about 20 percent by weight per unit volume of brine. The carotenoids are thought to protect the algae from sunlight. The concentration of carotenoids increases with increasing salt concentration of the brine up to the limit of halotolerance of the algae.

Numerous methods have been proposed for recovering beta carotene, carotenoids, and other valuable components from *Dunaliella salina*. *Dunaliella salina* provides a source of beta carotene and other carotenoids from which several nutritional supplements presently are manufactured. However, economically efficient recovery of carotenoids from *Dunaliella salina* in a form free from potentially toxic solvents and other undesirable substances has been somewhat problematic. Commercial exploitation of *Dunaliella salina* as a source of carotenoids presents numerous difficulties.

Halotolerant algae, including *Dunaliella salina* are typically found in salt lakes, including the Great Salt Lake in Utah. Harvesting *Dunaliella salina* from lakes and other natural settings typically is not commercially practicable, in part because of the low concentrations that are found in uncontrolled growing conditions.

Commercially, *Dunaliella salina* normally is harvested from cultures that are produced in specially constructed outdoor ponds. The outdoor ponds typically are constructed in regions with a hot and arid climate with little rainfall and few cloudy days to promote carotenoid production.

Two distinct methods of aquaculture have been developed for growing algae. These are an intensive mode and an extensive mode. Both aquacultural techniques require the addition of fertilizers to the medium to supply the necessary inorganic nutrients, phosphorous, nitrogen, iron, and trace metals, that are necessary for biomass production through photosynthesis.

The primary difference between the two modes of production is mixing of the growth medium. Intensive ponds employ mechanical mixing devices while extensive ponds rely on mixing by the wind. Therefore, factors that affect algae growth can be more accurately controlled in intensive aquaculture.

In both the intensive and extensive modes, the salinity of the growth medium is controlled within a specified range, usually between about 18 to 27 percent sodium chloride by weight per unit volume of brine. This range of concentrations is thought to provide the maximum carotenoid production. The optimum growth range for *Dunaliella salina* is said to be between about 18 and 21 percent salinity. Maximum carotenoid production in the algal biomass is said to occur at salinities greater than about 27 percent. Maximum carotenoid production per unit volume of the brine medium has been reported to occur at about 24 percent salinity.

Outdoor ponds for intensive aquaculture typically are somewhat expensive and are frequently constructed of concrete and lined with plastic. Brine depth generally is controlled at 20 centimeters, which has been considered to be the optimum depth for producing algal biomass. A number of configurations of the ponds have been proposed for intensive aquaculture. However, the open air raceway ponds are typically the most important commercially. Raceway ponds employ paddle wheels to provide mixing. Chemical and biological parameters are carefully controlled, including salt and fertilizer concentrations, pH of the brine, and purity of the culture.

Extensive aquaculture has been practiced in the hot and arid regions of Australia. Outdoor ponds for extensive aquaculture generally are larger than those for intensive aquaculture and normally are constructed in lake beds. The open air ponds are typically bounded by earthen dikes. No mixing devices are employed. Mixing in the pond is generated by the wind. Pond depth and chemical composition are optimized for maximum carotenoid production.

However, the parameters for maximum carotenoid production and culture purity and stability are not as easily controlled in the extensive ponds as in the intensive ponds because of the lack of efficient mixing and the larger volume of the extensive pond. The composition of the brine fluctuates. The algal biomass is less concentrated than in the intensive ponds. The extensive pond is more susceptible to infestations by predators and competitors.

Predators and competitors cannot typically survive at salinities of about 20 percent and above. If the salinity of the pond drops below about 20 percent, the culture may become infested with a predator that may rapidly increase in number and decimate the *Dunaliella salina* population. The primary predators are the ciliated protozoan *Fabrea salina* and the brine shrimp *Artemia salina*. At salt concentrations below about 15 percent, other algae tend to compete with *Dunaliella salina* for nutrients and additional predators may further reduce the *Dunaliella salina* population.

Recovery of the algae from the brine is more problematic in the extensive pond than in the intensive pond because of the more dilute culture. However, it has been observed that algae tend to concentrate in windows at the edges of extensive ponds and in natural salt lakes. The algae are often blown across the surface of the lake or pond where they collect and concentrate in windows at the lee side. It has been recognized that the ability to harvest the windows could significantly improve the process economics because of the higher concentration of algae. Nevertheless, satisfactory techniques for harvesting windows are not generally available.

It is not usually possible to consistently harvest windows from a fixed harvesting plant site. Wind direction normally is somewhat unpredictable and may change frequently. The windows may form at different locations along the side of the pond or lake. When the windrow does not form at a fixed harvesting plant site, then a dilute suspension that is depleted in the alga is processed, which results in a reduced production rate. Harvesting costs are higher due to the processing costs associated with more dilute cultures.

Nevertheless, higher harvesting costs may be offset by the capital costs associated with constructing concrete and plastic lined ponds for intensive aquaculture. Pond construction costs per unit volume for the earthen extensive ponds are significantly lower than those for the lined concrete ponds of intensive aquaculture.

It has been recognized that if algae could be harvested from the lakes in which they grow naturally, then pond construction costs, fertilizer costs, and brine make up costs conceivably could be substantially eliminated. However, harvesting algae from lakes and other natural settings typically has been considered uneconomical and without commercial utility. There usually is no degree of control over the salinity of the lake waters, the mineral and nutrient composition of the lake waters, and the degree of mixing in a natural salt lake. Dilute cultures of algae of questionable stability may occur.

Dilute cultures of *Dunaliella salina* are generally uneconomical to process in part because of the problems and difficulties encountered in separating the algae from the brine in which they grow. The algae have mobility, neutral density, and a small elliptical shape of approximately 12 to 16 microns by 25 microns that makes the algae somewhat difficult to harvest.

*Dunaliella salina* typically is separated from the brine within which it is found by using a chemical flocculating or coagulating agent in combination with a settler, centrifuge, filter, adsorbent, or other separation means. Chemical treatments, including, for example, the silanes, can be applied to adsorption media to enhance adsorption. Various processes have been proposed for extracting beta carotene, carotenoids, and other valuable components from the algae, including glycerol and proteins. Hydrocarbon solvents, edible oil solvents, and supercritical carbon dioxide have been proposed as solvents for the extractions. The algae may be disintegrated by mechanical means to promote extraction of the components.

Chemical additives such as flocculants and coagulants have limited the commercial exploitation of *Dunaliella salina* as a source of carotenoids and beta carotene in part because of the costs of adding these components to algal suspensions, particularly dilute suspensions. Chemical additives, chemical treatments, and hydrocarbon solvents are considered undesirable in nutritional supplements.

It would be desirable to more economically and efficiently harvest *Dunaliella salina* and to extract the carotenoids and other valuable components therefrom with minimal or no undesirable additives.

SUMMARY OF THE INVENTION

The invention provides a process for separating micro algae from the medium in which they grow for the subsequent recovery of components from the algae. The process includes adsorptive bubble separation methods that are capable of dewatering the algae and achieving concentrations of algae from which extractable components can be economically extracted. Extractable concentrations can be achieved from a wide range of initial concentrations. Chemical additives and treatments can be avoided that could contaminate the growth medium or the algal concentrate. The growth medium and algal residue can be returned to the source after extraction of components, if desired.

The invention is capable of economically dewatering algae obtained from the dilute suspensions found in naturally occurring lakes and ponds. Cell concentrations in dilute suspensions sometimes are as low as 2,000 cells per milliliter of growth medium. Multiple adsorptive bubble separation units can be used to dewater the algae. The algae become more and more concentrated in subsequent adsorptive bubble separation steps.

The invention can be applied to the harvesting of windows and includes a mobile harvesting process plant. In one aspect, the adsorptive bubble separation methods use pneumatic froth flotation devices that can be produced from light weight plastics and have a small footprint area. Because of the small footprint, the equipment can be mounted on a flatbed truck, trailer, raft, or other easily maneuverable transport device that is readily moved to the site of windrow formation. The equipment can go to the windrow, rather than waiting for the windrow to come to the equipment.

The invention is also capable of economically dewatering the more concentrated suspensions found in cultivated extensive and intensive ponds, where cell counts sometimes reach into the millions of cells per milliliter of growth medium.

The process comprises several steps. First, a suspension of algae in their growth medium is obtained from a source, which may include an intensive pond, an extensive pond, or a naturally occurring lake, including the brines of the Great Salt Lake in Utah in which *Dunaliella salina* thrives. After the algal suspension has been obtained, it may be separated from the aqueous medium by adsorptive bubble separation.

In one aspect, the invention includes dispersed gas flotation methods generally, including mechanical and pneumatic froth flotation methods, dissolved gas flotation methods, and electrolytic methods for dewatering algal suspensions of algae of the genus Dunaliella and extracting components from the algae in the absence of undesirable chemical additives or treatments. Food grade solvents may be used that result in high recoveries of mixed carotenoids from Dunaliella.

Electrolytic and dissolved gas flotation are not necessarily equivalent to dispersed gas flotation. When the aqueous medium is concentrated brine, then more current is needed for the electrolytic flotation technique because brine is more conductive than fresh water. Gases typically do not dissolve as readily in concentrated brine as in fresh water.

*Dunaliella salina* can be dewatered by rupturing the membrane that encapsulates the algal bodies and then removing the water by an adsorptive bubble process in the absence of coagulents or flocculating agents. While not wishing to be bound by theory, it is believed that when the membrane encapsulating the algal body ruptures, then the algal body adsorbs on hydrophobic gas bubbles that are intimately contacted with the brine. High shear conditions can be used that typically could be expected to disrupt a floc of algal bodies and would be considered undesirable where the process was directed to floating flocculated bodies. The algae also appear to contain naturally occurring surface active agents of sufficient concentration and power to readily produce a stable froth. Several rupturing methods are discussed below in the Detailed Description.

In froth flotation, which is a subset of dispersed gas flotation, a gas is dispersed into fine bubbles. The gas can be air or a gas that does not contain oxygen or oxidizing agents to avoid oxidation of the carotenoids. The fine bubbles and the algal suspension are intimately contacted to adsorb the algae onto the surfaces of the bubbles and to form bubble and alga agglomerates and a brine that is depleted in the algae. The bubble and alga agglomerates are separated from the liquid phase as a concentrated froth of algal suspension.

Flotation aids can be used to enhance recovery, if desired. Flocculating or coagulating agents are not required, at least for dewatering *Dunaliella salina* in brine, but may be used if desired. The ruptured algae are floated by attachment to the gas bubbles, not by flocculation. A high shear field can be employed to provide small bubbles and to provide intimate bubble and particle contact, whereas in flocculation and flotation processes, low shear fields typically are used to minimize floc breakage.

The gas for froth flotation can be dispersed into fine bubbles by generating a liquid jet of the algal suspension and plunging the liquid jet through the gas and into a dispersion of the gas in the algal suspension. The Jameson cell, which is described below in the Detailed Description, is one apparatus that may be used in connection with this aspect of the invention.

The gas can be dispersed into fine bubbles by sparging the gas into the liquid phase, as in a column. A multi-stage loop flow flotation column, sometimes called the "MSTLFLO" column, is one apparatus useful in practicing this aspect of the invention.

The gas can be dispersed into fine bubbles by introducing the gas into the algal suspension and mechanically shearing the suspension and the gas. The gas can be dispersed into fine bubbles by introducing the gas into a liquid in turbulent, high velocity flow, including a static mixer for generating small bubbles. Typically, the liquid would be fresh water, brine, or a surfactant solution.

Combinations of the above and other apparatus for generating small bubbles and providing intimate contact between the bubbles and the algal suspension should be useful, depending on the circumstances and the available equipment.

Intimate contact between fine bubbles and the algal suspension can be accomplished in several ways. The bubbles and suspension can be mechanically or pneumatically mixed. Mechanical mixing devices typically employ a rotating impeller on an upright shaft to provide mechanical mixing and aeration. Aeration can also be provided through the use of blowers.

Pneumatic mixing relies upon the addition of a gas to the two phase system of gas bubbles and algal suspension to create a density difference that results in mixing. The bubbles and algal suspension can be contacted in either countercurrent or cocurrent flow or combinations thereof in each method.

The adsorptive bubble separation steps typically are repeated to further concentrate the algal suspension. A concentration is obtained of algae in the suspension suitable for extraction of extractable components from the algae, including extraction of mixed carotenoids from *Dunaliella salina*.

In another aspect of the invention, the method includes filtering the algal suspension. The algal suspension can be contacted with deep bed filtration media or can be passed across a filtration membrane, as in microfiltration. Filtering by deep bed filtration usually takes place as a preconcentration step prior to an adsorptive bubble separation process. The algae typically are ruptured prior to filtration, usually by passing the algal suspension through a sufficient pressure drop, although any of the rupture methods discussed in the Detailed Description below should suffice. Microfiltration typically is useful as a post concentration step performed after an adsorptive bubble separation process to obtain a concentration of algae suitable for dense gas extraction of algal components.

In another aspect, the invention includes extracting components from the dewatered algal suspension by contacting the dewatered suspension with a suitable solvent. The solvent can be predispersed in the algal suspension for a subsequent extraction, if desired. Extraction solvents suitable for use in the practice of the invention include edible oils, flavorants, petrochemical solvents, and dense gases, although not necessarily with equivalent results. Flavorants, which are generally recognized as safe, typically have excellent qualities as extraction solvents and are less viscous, easier to use, and have greater solvent power than edible oils. Petrochemical solvents usually are not desirable in connection with nutritional supplements and are often avoided for this reason.

If a suitable concentration of algae in the suspension has been obtained, then extraction may be accomplished with dense gases, if desired, including supercritical and subcritical carbon dioxide and other gases. Typically, the algae are concentrated after froth flotation by passing across a microfiltration membrane to obtain a retentate concentration suitable for extraction of components with dense gases. However, more conventional extraction methods may also be used, if desired, with or without a microfiltration step.

Thus, the invention provides, among other things, more economically efficient, environmentally sound, and nutritionally acceptable methods as compared to typical prior methods for harvesting and dewatering *Dunaliella salina* and for extracting mixed carotenoids from the algae. Harvesting can be accomplished from dilute concentrations, windows, or more concentrated sources. Mobile harvesting equipment can be used, if desired. Dewatering can be accomplished by adsorptive bubble separation in the absence of flocculants, coagulants, or other undesirable additives. Beta carotene and other carotenoids can be extracted from the concentrated algae with food grade solvents to produce edible sources of mixed carotenoids.

BRIEF DESCRIPTION OF THE DRAWINGS

Some of the features and advantages of the invention have been stated. Other advantages will become apparent as the description of the invention proceeds, taken in conjunction with the accompanying drawings, in which.

DETAILED DESCRIPTION

Figure 1:
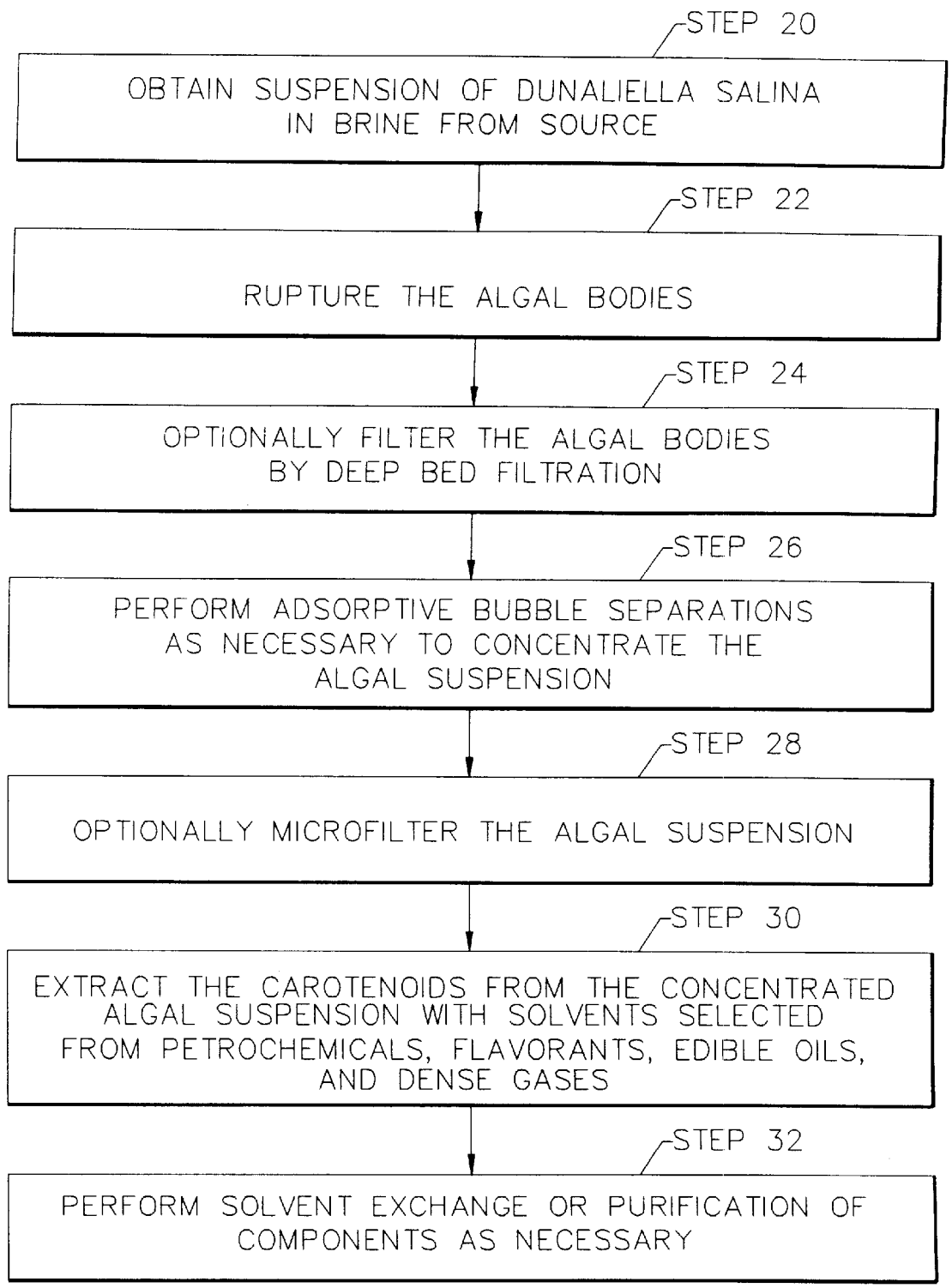
FIG. 1 represents a flow diagram of a process for obtaining a suspension of algae, dewatering the algae, and extracting components from the algae.

The steps of a generalized process in accordance with the invention for separating algae from the medium in which they are growing is represented in FIG. 1. FIG. 1 is discussed below with reference to dewatering a brine containing the alga *Dunaliella salina* for the purpose of extracting mixed carotenoids from *Dunaliella salina*.

*Dunaliella salina* may be somewhat unique among the various algae in that it typically occurs as a single-celled chlorophyll-containing organism that does not have a true cell wall. Instead, *Dunaliella salina* may be considered to have a protective phospholipid membrane that is ruptured in the practice of the invention. It is believed that the internal components of the algal body, and not the membrane, are largely responsible for the favorable surface active behavior of *Dunaliella salina* in brine under conditions of adsorptive bubble separation.

It should be recognized that the genus Dunaliella is believed to include the species *Duniella bardawil* and that the invention as described herein is believed to be fully applicable to *Dunaliella bardawil*. There may be some confusion in the literature regarding the taxonomy of Dunaliella, and it is possible that *Dunaliella salina* and *Dunaliella bardawil* are one and the same.

However, it should be recognized that there are other algae, both fresh and salt water algae, that may be dewatered by practice of aspects of the present invention, although not necessarily with equivalent results. It should be recognized that other algae may include desirable components, including carotenoids, proteins, and other organic compounds that may be extractable in accordance with the invention, if desired, although again not necessarily with equivalent results. Aspects of the invention are believed to be applicable to algae of the phyla Chlorophyta and Rhodophyta generally.

The following outline sets forth the remaining portions of the detailed description and the examples for the convenience of the reader.

I. Harvesting the Algae
II. Rupturing the Algal Cells
III. Chemical Aids and Chemical Treatments Optional, but not Usually Necessary
IV. Mechanical Filtration to Separate Algae from Growth Medium
V. Adsorptive Bubble Separation to Dewater Algae
   A. General Considerations
   B. Froth Flotation
   C. Froth Flotation Circuits
      1. Roughing
      2. Concentrating
      3. Scavenging
   D. Mechanical and Pneumatic Flotation Cells in General
      1. Mechanical Flotation Cells
      2. Pneumatic Flotation Cells
         a. The Jameson Cell
         b. Multistage Loop-Flow Flotation Column (MSTLFLO)
         c. Canadian Column
         d. Air-Sparged Hydrocyclone (ASH)
         e. EKOFLOT Pneumatic Flotation Cell
         f. Microcel™ Microbubble Flotation Column
         g. Other Flotation Devices
   E. Advantageous Froth Flotation Circuit
VI. Recovering Selected Components from Concentrated Algal Suspensions
   A. Purifying and Separating the Components
   B. Beta Carotene and Other Carotenoids
   C. Products and Applications
   D. Glycerol, Protein, and Other Components
VII. Examples
   A. Cell Rupture in a Pump Loop
   B. Deep Bed Filtration
   C. Microfiltration
   D. Froth Flotation
      1. Mechanical Froth Flotation
      2. Pneumatic Froth Flotation
         a. Jameson Cell
         b. Multistage Loop-Flow Froth Flotation Column (MSTLFLO)
         c. Canadian Column
         d. Air Sparged Hydrocyclone (ASH)
   E. Recovery of Valuable Components
      1. Solvent Distribution Coefficients
      2. Liquid Extraction
      3. Liquid Extraction Mass Transfer Kinetics
      4. Continuous Extraction of Carotenoids with Limonene I. Harvesting the Algae Returning to FIG. 1, a feed stream comprising a suspension of *Dunaliella salina* in brine is obtained from a source thereof in accordance with step 20. The feed stream typically will be obtained by pumping an algal suspension from the source to the equipment that is used for dewatering the algae. Generally, a centrifugal pump will be used to harvest the algae, although other pumps may be substituted. The centrifugal pump is one of the most widely used pumps in the chemical industry for transferring liquids of all types.

It is sometimes desirable that a mobile harvesting pump is used to transfer the algal suspension from the source to the dewatering equipment. In this manner, the invention can be applied to the harvesting of windows. The pump can be a floating pump or a submersible pump or may be mounted on a raft or other device that is easily locatable at the site of windrow formation.

The dewatering methods of the invention primarily rely on the use of froth flotation columns that have a small footprint area. Because of the small footprint, the equipment can be mounted on a flatbed truck, trailer, raft, or other easily maneuverable transport device that is readily moved to or near the pumping site for receiving the feed stream. The equipment can go to the harvesting site, rather than waiting for the harvesting site to come to the equipment.

The algal suspension that is obtained for the feed steam can vary over a wide range of concentrations, from dilute suspensions to more concentrated suspensions. The invention is capable of dewatering dilute suspensions found in naturally occurring lakes and ponds. For example, the invention is useful for harvesting and dewatering suspensions of native populations of *Dunaliella salina* obtained from the Great Salt Lake in Utah.

Cell concentrations in dilute suspensions sometimes are as low as 2,000 cells per milliliter of growth medium. Use of a mobile harvesting pump can improve the economics of obtaining algal suspensions because the mobile harvesting pump can go to the location where windows are formed.

The invention is capable of economically dewatering the more concentrated suspensions found in cultivated extensive and intensive ponds, where cell counts sometimes reach into the millions of cells per milliliter of growth medium.

II. Rupturing the Algal Cells

Typically, it is useful to rupture the *Dunaliella salina* cells prior to dewatering the suspension, whether by adsorptive bubble separation or deep bed filtration, as shown in step 22 of FIG. 1. High recoveries have been observed for ruptured cells over the range of 0.0003 milligrams of mixed carotenoids per milliliter of suspension to 0.3 milligrams of mixed carotenoids per milliliter. This range corresponds to about 2,000 to 3,000,000 algal cells per milliliter.

Rupturing the cells may be performed in the presence of air, but is advantageously performed in the absence of oxygen or oxidizing agents to minimize exposure of the ruptured cell components to oxygen. Oxidation of valuable compounds, including carotenoids can be substantially eliminated. Suitable gases include those inert to the algal cell components, including nitrogen, carbon dioxide, argon and other noble gases, which are generally considered to be chemically inert, and mixtures of these gases.

Rupturing the cells prior to pneumatic froth flotation is necessary to recover carotenoids. However, it should be understood that pneumatic flotation devices can be operated at conditions that will rupture the cells, as discussed below, so that a separate prior rupturing step is not required. The cells tend to rupture in the shear field created by the rotor and stator mechanism of mechanical froth flotation devices. Recoveries of greater than ninety-five percent of available cells have been obtained for feeding intact cells to a mechanical froth flotation device. If deep bed filtration is used to concentrate the algal suspension, either before or after an adsorptive bubble separation process, then rupturing the cells typically is necessary if the deep bed is to efficiently trap the algal bodies.

Any suitable means may be used to rupture the cells. The cells may be ruptured by mechanical means, including a high shear mixer and a French press. The cells may be ruptured by circulating the suspension through a valve in a pump loop.

The algal cells can also be ruptured by passing the algal suspension at high pressure through a Jameson cell as a first stage dewatering step. The Jameson cell and its operation to rupture the cells is discussed below in connection with froth flotation techniques for dewatering the algal suspension. A separate rupturing step can be avoided by rupturing the algae in a Jameson cell.

Circulating the suspension through a pump loop can easily be accomplished by recycling some portion of the feed through the harvesting pump that is used to transport the brine from the source to the dewatering equipment.

Figure 2:
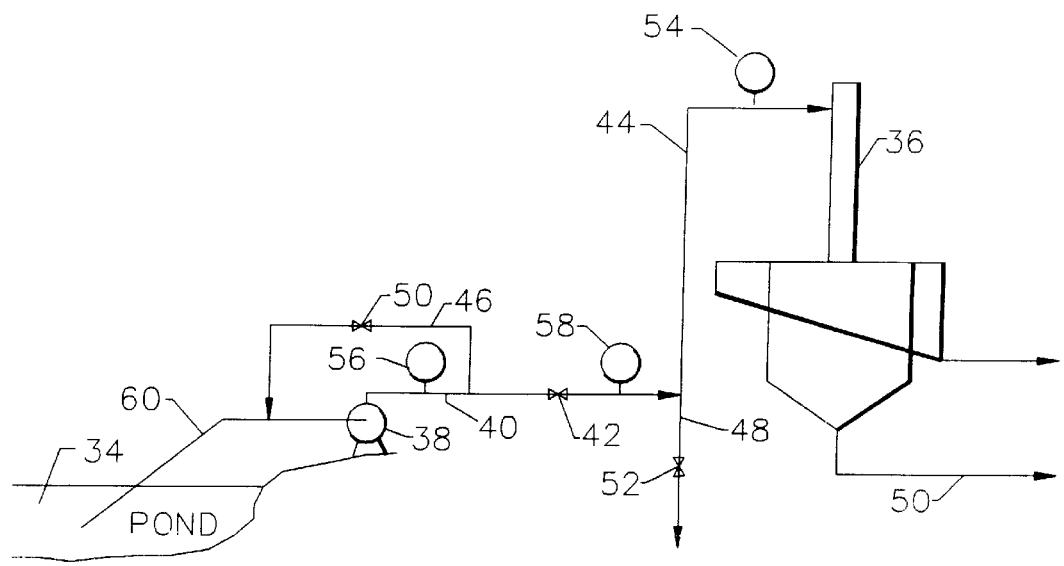
FIG. 2 is a schematic representation of a pump loop for rupturing the algal bodies.

Apparatus for rupturing the algal cells by circulating the suspension through a valve in a pump loop is illustrated in FIG. 2. FIG. 2 is discussed in the Examples below, which show how the pressure drop and percent recycle are determined for rupturing the algal cells in a pump loop.

As illustrated in FIG. 2, the algal suspension is transported from a source 34 to a dewatering device 36 through a pump 38, which may be a centrifugal pump. A pump discharge line 40 supplies brine to the dewatering device. A throttling valve 42 in the pump discharge line is provided for adjusting the pressure drop. The brine enters the dewatering device through feed inlet line 44. A recirculating line 46 is provided for recirculating brine from the discharge side to the intake side of the pump. The flow rate through the recirculating line is varied as necessary to provide the desired percent recycle through valve 50 in the pump loop.

Two parameters control the number of cells that are ruptured by passing the algal suspension through a pressure drop. The first parameter is the magnitude of the pressure drop. The second parameter is the number of passes through the pressure drop. The percent of algae ruptured increases with increasing pressure drop and percent recycle. Multiple passes are required to achieve greater than forty percent cell rupture at pressure drops of less than about 200 psig. However, there appears to be only a small benefit to operating at a pressure drop greater than about 150 psig when the percent recycle is greater than about 100 percent. Multiple passes through the pressure drop increase the percent of ruptured cells.

It has been determined to be useful to rupture *Dunaliella salina* by passing an algal suspension through a pressure drop provided by a pump loop where the pressure drop is from about 50 to 200 psig with from about 100 to 300 percent recycle. It has also been determined that a pressure drop of from about 100 to 150 psig with about 200 to 300 percent recycle is useful.

III. Chemical Aids and Chemical Treatments Optional, but not Usually Necessary

Chemical aids and chemical treatments for harvesting and dewatering algae are usually undesirable for a variety of reasons as addressed below, especially where products obtained from the algae are to be used in nutritional supplements. It should be emphasized that chemical aids and treatments normally are not needed in the practice of the invention. Chemical aids and treatments for dewatering can be avoided by practicing the cell rupture techniques described herein in connection with the other aspects of the invention. Nevertheless, chemical aids and treatments can be employed as an option, if desired.

Chemical aids may be added to the algal suspension for a variety of purposes as desired or needed prior to dewatering. Chemical aids added to improve separation efficiency may be classified into three categories: agglomerating agents, surface modifying agents, and predispersed solvents. Solvents that are used in connection with downstream extraction steps for recovering carotenoids can be dispersed in the algal suspension at some point prior to the extraction step, including prior to dewatering the suspension. These solvents are said to be "predispersed." Solvents, including predispersed solvents, are discussed below in connection with the extraction steps of the invention. Agglomerating agents such as ionic coagulants and polymeric flocculants may be added to generate larger aggregates that are more easily separated. Surface modifying agents such as frothers and collectors may be added to render the algae more floatable.

Chemical aids could be added in a mixing device after cell rupture and before adsorptive bubble separation. However, it normally is not necessary in accordance with practice of the invention to employ undesirable chemical aids to dewater *Dunaliella salina*. The cell rupture techniques practiced in accordance with the invention are sufficient to enable dewatering of the algae.

Chemical aids can adversely affect the quality and value of the nutritional supplements prepared from algal components and of the medium in which the algae are grown. Some chemical additives may not be desirable in processes for producing nutritional supplements. Disposal problems can arise from the use of chemical aids respecting the algal growth medium and algal residue. For example, undesirable chemical aids are to be avoided in dewatering algal suspensions obtained from the Great Salt Lake when the brine is to be returned to the lake.

Some chemical aids may be undesirable from an economic standpoint. Large quantities of chemicals, such as alum, are required to coagulate the algal bodies when the algae are obtained from relatively dilute suspensions found in natural lakes and some extensive ponds. Typically, a subsequent separation process is needed to separate the chemical additive from the algal bodies, which further increases production cost.

Although not normally necessary, it may be considered desirable to use a frother to enhance recovery of the algae in froth flotation processes. A frother may be added to the gas or liquid phase prior to entering the froth flotation device or may be added directly to the algal suspension in the froth flotation device to increase the stability of the froth and to generate small bubbles. Examples of frothers include 2-ethyl hexanol, methyl isobutyl carbinol, which is also known as MIBC, and Dowfroth 250. Dowfroth 250 is a frother that is commercially available from the Dow Chemical Company, which is located in Midland, Michigan. When a frother is used, then the frother dosage varies somewhat depending on the manner in which the algal suspension is dewatered. Typically, the frother dosage ranges from about 5 to 25 ppm.

However, it should be emphasized that no frothers normally are required for the recovery of carotenoids from *Dunaliella salina*. While not wishing to be bound by theory, it is believed that the algae contain compounds of sufficient concentration and surfactant power to generate small bubbles in a saturated brine.

The algae in the feed stream may be conditioned with collectors and depressors to improve the selectivity of the flotation. For example, it may be desirable to increase the selectivity of the bubbles to adsorb *Dunaliella salina* in preference to halotolerant bacteria or other undesirable competitive algae or predators. Collectors unite with the algal bodies and attach or adsorb them to the bubble surface so that the algal body can be removed with the bubble. On the other hand, depressors unite with the undesirable components present in the suspension to substantially preclude their attachment to a bubble. Use of depressors may be desirable where substantial contaminants would otherwise be recovered with the algae.

Agglomerating agents include synthetic polymers and ionic coagulants. Ionic coagulants typically include alum or ferric chloride. Generally, it is desirable to avoid agglomerating agents. Agglomerating agents are not considered necessary in the practice of the invention. However, they may be determined to be of benefit in various aspects of the invention, depending on the circumstances, and can be used to advantage. For example, recovery of algal components from deep bed filtration media sometimes can be improved by the use of agglomerating agents.

IV. Mechanical Filtration to Separate Alga from Growth Medium

Returning to FIG. 1, the process of the invention optionally can include various filtration steps. A mechanical filtration step is useful both before and after adsorptive bubble separation of the algae from the brine, as shown in steps 24 and 28, respectively. Typically, the algal suspension can be concentrated prior to adsorptive bubble separation by using deep bed filtration. The algal suspension can be concentrated after adsorptive bubble separation by microfiltration. However, it should be recognized that any of these filtration steps can be performed either before or after adsorptive bubble separation and that, in some cases, adsorptive bubble separation may not be necessary. However, adsorptive bubble separation typically provides the most economical means for sufficiently concentrating the algal suspension to obtain its components.

Deep bed filtration is a technique useful to concentrate the algal suspension up to an economically practical limit of about 1 percent solids in the feed. Beyond this limit, deep bed filtration may be somewhat uneconomical. Backwashing to remove solids from the filter media becomes more and more frequent as the solids concentration increases. The pressure under which the filter is operated to force the liquid through the column becomes greater. For this reason, deep bed filtration typically is useful to concentrate the algal suspension prior to adsorptive bubble separation, and is somewhat less useful after adsorptive bubble separation is completed.

Deep bed filtration relies upon a bed of granular media, usually sand, through which the algal suspension flows downward under gravity. The algae are deposited in the pores of the granular media and in the interstitial spaces between the grains of media.

Deep bed filtration should not be confused with straining filtration. Straining takes place on the surface of a mesh or fabric. However, deep bed filters retain particles throughout their volume, with each pore and void space having a probability of retaining algal cells from the suspension that is flowing through.

Suitable deep bed filtration media include those typically used in commercial processes, such as quartz sand, garnet sand, anthracite, fiberglass, and mixtures thereof. The media can be washed with fresh water or brine to recover the algal cells for further concentration of valuable components by adsorptive bubble separation.

The media may also be contacted with a solvent to recover the valuable components from the trapped algal cells. The solvents discussed below in connection with extraction of carotenoids from *Dunaliella salina* should be useful for extraction of similar components from algal bodies in a deep bed filter.

Either intact cells or components of ruptured cells may be recovered by the deep bed filter. Intact cells could be recovered by flocculating the cells prior to filtration. However, recovery typically is considerably improved if the cells are ruptured prior to filtering. Greater than 70 percent recovery of carotenoids has been achieved by practice of the invention for algal feed suspensions containing at least 0.002 milligrams of carotenoids per milliliter of brine. An example of the use of a deep bed filter in the practice of the invention is shown in the Examples.

It may be useful for some extraction processes or for other reasons to increase the concentration of carotenoids in *Dunaliella salina* beyond the practical limits of deep bed filtration or adsorptive bubble separation processes. Typically, adsorptive bubble separation processes have a practical upper limit for the maximum concentration of carotenoids of less than about 10,000 ppm. The carotenoid concentration in an algal suspension should be greater than about 10,000 ppm for some purification processes to be economically viable, including dense gas extraction.

Figure 3:
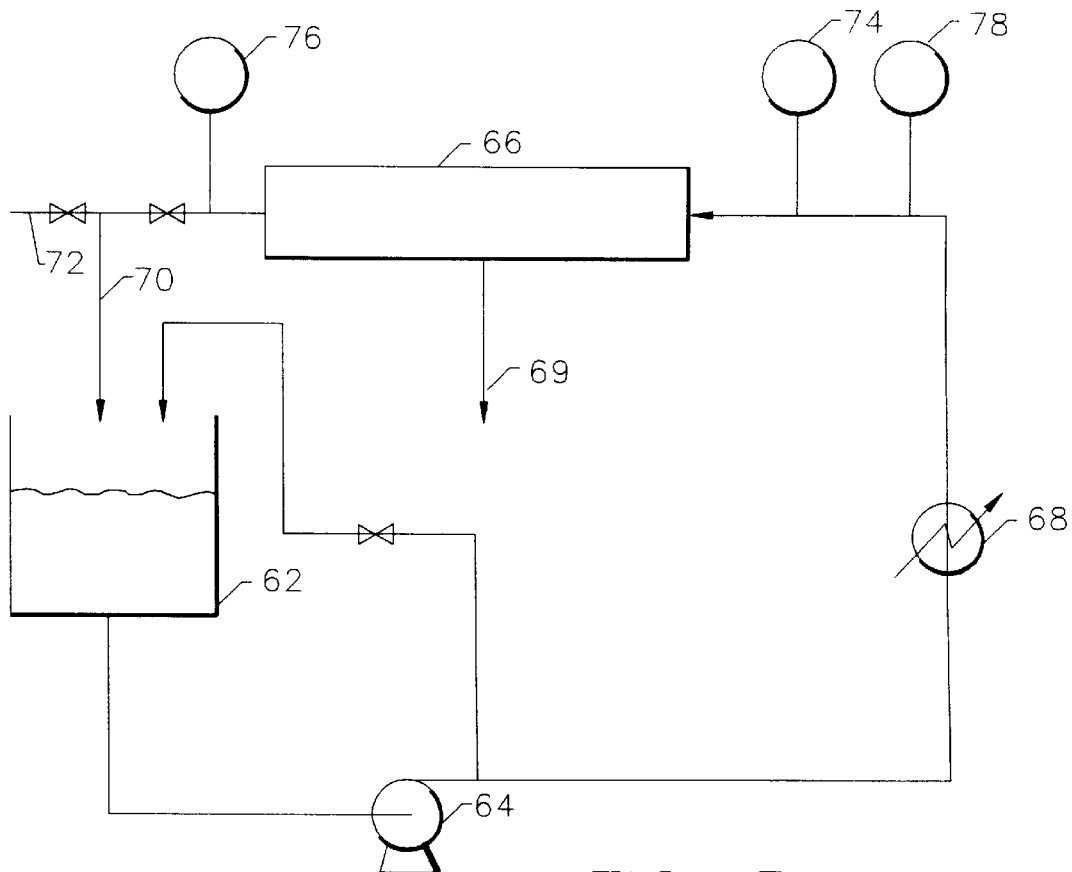
FIG. 3 is a schematic representation of a circuit for cross flow microfiltration of an algal suspension.

Microfiltration has been determined to increase the carotenoid concentration in a suspension of *Dunaliella salina* in brine beyond that normally obtainable by adsorptive bubble separation by an order of magnitude with no measurable loss of carotenoids in the permeate. Concentrations of up to about 20,000 ppm have been obtained by the practice of microfiltration in connection with the practice of the invention. A schematic of a cross flow microfiltration process is represented in FIG. 3. Microfiltration using the apparatus of FIG. 3 is shown in the Examples, at VII C.

As represented in FIG. 3, a suspension of *Dunaliella salina* in brine, which could be obtained from, for example, a froth flotation cell, is charged to a holding tank 62. The suspension is transferred through a pump 64 to a cross flow microfilter 66. Optionally, a heat exchanger 68 may be provided to cool the suspension prior to entering the filter. The microfilter is equipped with a porous membrane along which the algal suspension is pumped. A typical membrane may comprise ceramic materials, including, for example, zirconium oxide, and usually will have an absolute rating of less than 10 microns.

The membrane is typically in the configuration of a cylinder and the suspension is pumped through the cylinder. The brine passes through the membrane and is removed as permeate through line 69. The algal bodies remain in suspension and pass through the cylinder as retentate through line 70. The retentate may be returned to the holding tank and circulated through the filter several times until a sufficient concentration has been obtained. Alternatively, the retentate may be sent to another stage of microfiltration or directly to an extractor through line 72.

The carotenoid globules usually are less than one tenth of a micron in diameter and significant losses normally would be expected in the permeate. The algal bodies in suspensions obtained from froth flotation devices typically have been ruptured and the suspensions are somewhat gelatinous and would normally be expected to rapidly foul the membrane. Nevertheless, by practicing the process of the invention, carotenoids typically are not detectable in the permeate and, after an initial drop in flux, the flux across the membrane remains substantially constant without an increase in pressure drop.

Figure 4:
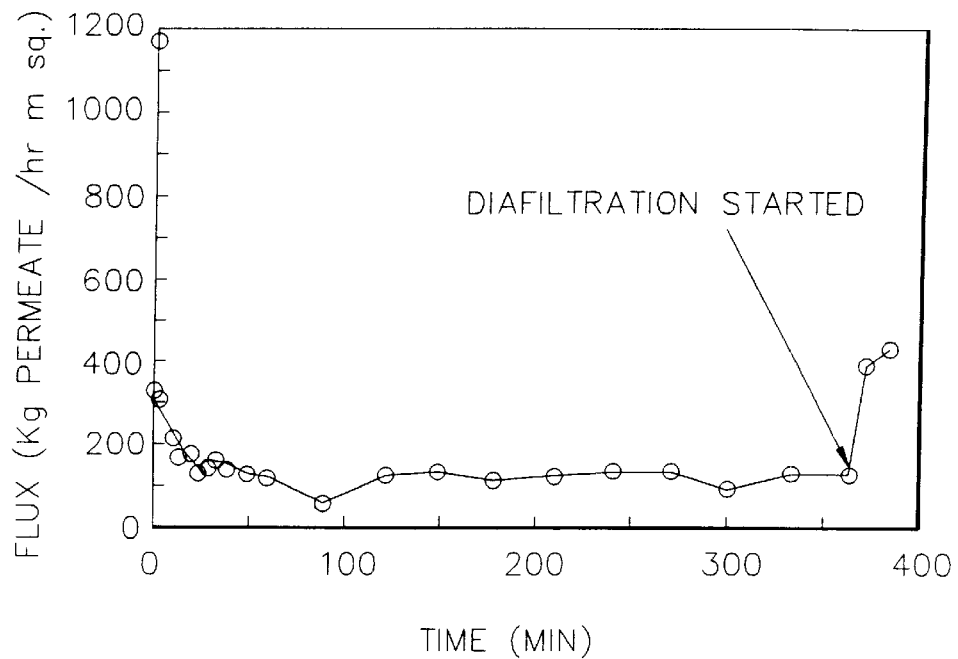
FIG. 4 is a graphical representation of flux over time for the cross flow microfiltration circuit of FIG. 3.

Fresh water may be added to either the feed or the retentate to reduce salt concentration in the suspension. Additional filtration and dilution steps may be added as needed to achieve a desired final salt and carotenoid concentration in the retentate. Dilution followed by filtration is sometimes called "diafiltration." A plot of flux versus time is shown in FIG. 4 for microfiltration and diafiltration and is discussed below in connection with the Examples.

V. Adsorptive Bubble Separation to Dewater Algae

A. General Considerations

Returning now to FIG. 1, after the algal cells are ruptured in accordance with step 22 and the optional filtration steps 24 and 28 are performed, if any, then in accordance with step 26, adsorptive bubble separations are performed as necessary to concentrate the algal suspension.

Adsorptive bubble separation is based on the selective adsorption of algal cell material to the surfaces of gas bubbles passing through the algal suspension. Bubbles rise to form a froth that carries the algal material off, typically overhead. Adsorptive bubble separation methods are suitable for removing small amounts of the algae from large amounts of brine.

There are a variety of adsorptive bubble separation techniques, in some of which a froth is generated and in some of which no froth is generated. One useful adsorptive bubble separation technique for dewatering algae is a dispersed gas flotation technique termed "froth flotation." A schematic of a generalized froth flotation technique in which gas is dispersed into a liquid is shown in FIG. 5.

Other adsorptive bubble separation techniques that may be useful in the practice of the current invention are electrolytic flotation and dissolved gas flotation. However, it should be recognized that there are practical limits on these processes and that they are not necessarily equivalent to dispersed gas flotation. In electrolytic flotation, bubbles are generated by passing an electric current through the aqueous medium that is to be separated from the algae. If the aqueous medium is concentrated brine, then a relatively larger current may be needed to generate the bubbles. In dissolved gas flotation, the gas is dissolved in a portion of the feed stream, under pressure in a separate vessel, and the resulting mixture is then introduced into the flotation vessel. The sudden drop in pressure causes the dissolved gas to nucleate and form small bubbles. The solubility of air in brine is somewhat limited and so another, more soluble gas that does not adversely affect carotenoids may be selected, including, for example, helium.

B. Froth Flotation

Figure 5:
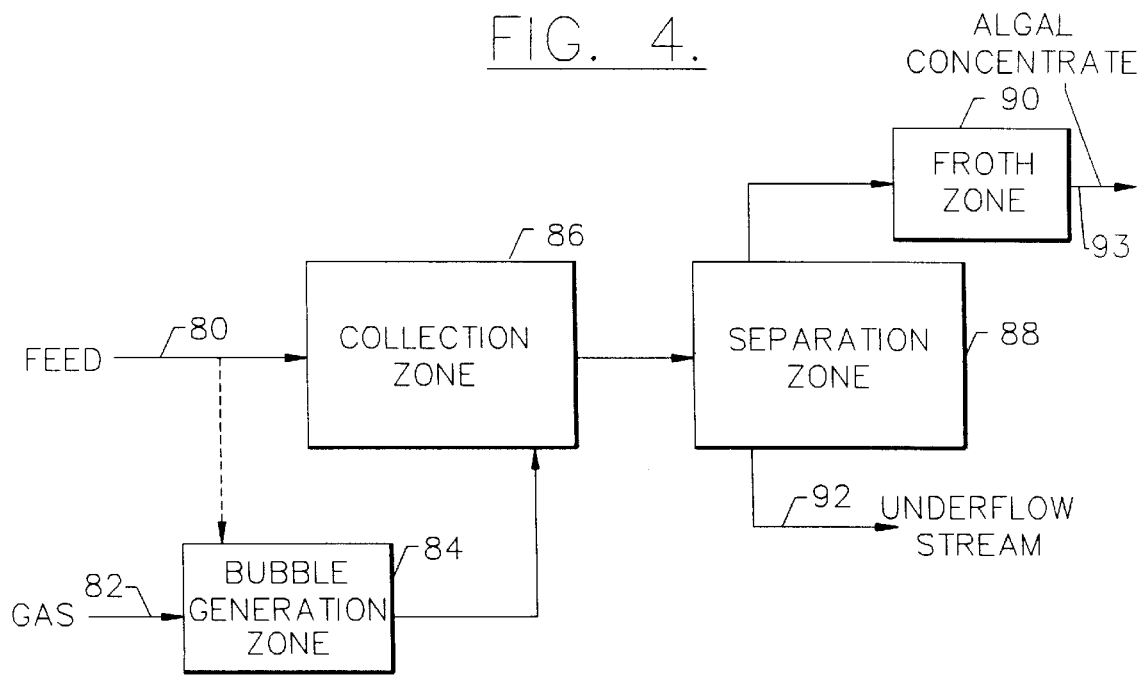
FIG. 5 is a schematic representation of a froth flotation process describing the various zones of a froth flotation process.

As shown in FIG. 5, the froth flotation device includes a bubble generation zone 84, a collection zone 86, a separation zone 88, and a froth zone 90. Some or all of these zones may or may not occupy the same vessel. Feed stream 80 enters the froth flotation device at either the collection zone 86 or the bubble generation zone 84, depending on the equipment chosen. In either event, a gas is dispersed through the bubble generation zone in the algal suspension in the collection zone to produce a two phase dispersion of gas in liquid. It is desirable to produce a large number of small bubbles to maximize the surface area of gas available for collision with algal bodies in a given volume of the algal suspension.

In the collection zone the algal suspension is contacted with fine bubbles under conditions that promote intimate contact. The bubbles collide with the algal bodies and form bubble and alga agglomerates. It is desirable to generate intense mixing in the collection zone to provide a high frequency of collisions.

After the bubble and alga agglomerates are formed in the collection zone, they are then separated from the brine depleted in algae in the separation zone 88, typically by gravity. The density of the gas is two to three orders of magnitude less than that of the brine. The density difference promotes floating of the bubble and alga agglomerates to the surface of the gas and liquid dispersion, where the agglomerates accumulate as froth in the froth zone 90.

The froth, enriched in carotenoids, overflows the froth zone as stream 93. A collection launder, as shown at 122 in FIG. 6, typically receives the froth zone overflow, where the froth is collapsed. The underflow stream 92, which is the brine depleted in algae, underflows the flotation device and may be recycled or discarded.

Suitable gases for use in adsorptive bubble separation devices should be non-toxic and non-hazardous, including air, nitrogen, carbon dioxide, helium, argon and other noble gases, which are generally considered chemically inert, and mixtures thereof. An inert gas that does not contain oxygen or oxidizing agents is particularly useful to avoid oxidation of the carotenoids present in the cell mass.

C. Froth Flotation Circuits

The froth flotation devices may be used in a flotation circuit to maximize recovery and concentration of the valuable components present in the algae. The relatively high energy costs for the flotation process are compensated for by the high recovery and concentration factors that may be achieved by using a flotation circuit.

Figure 6:
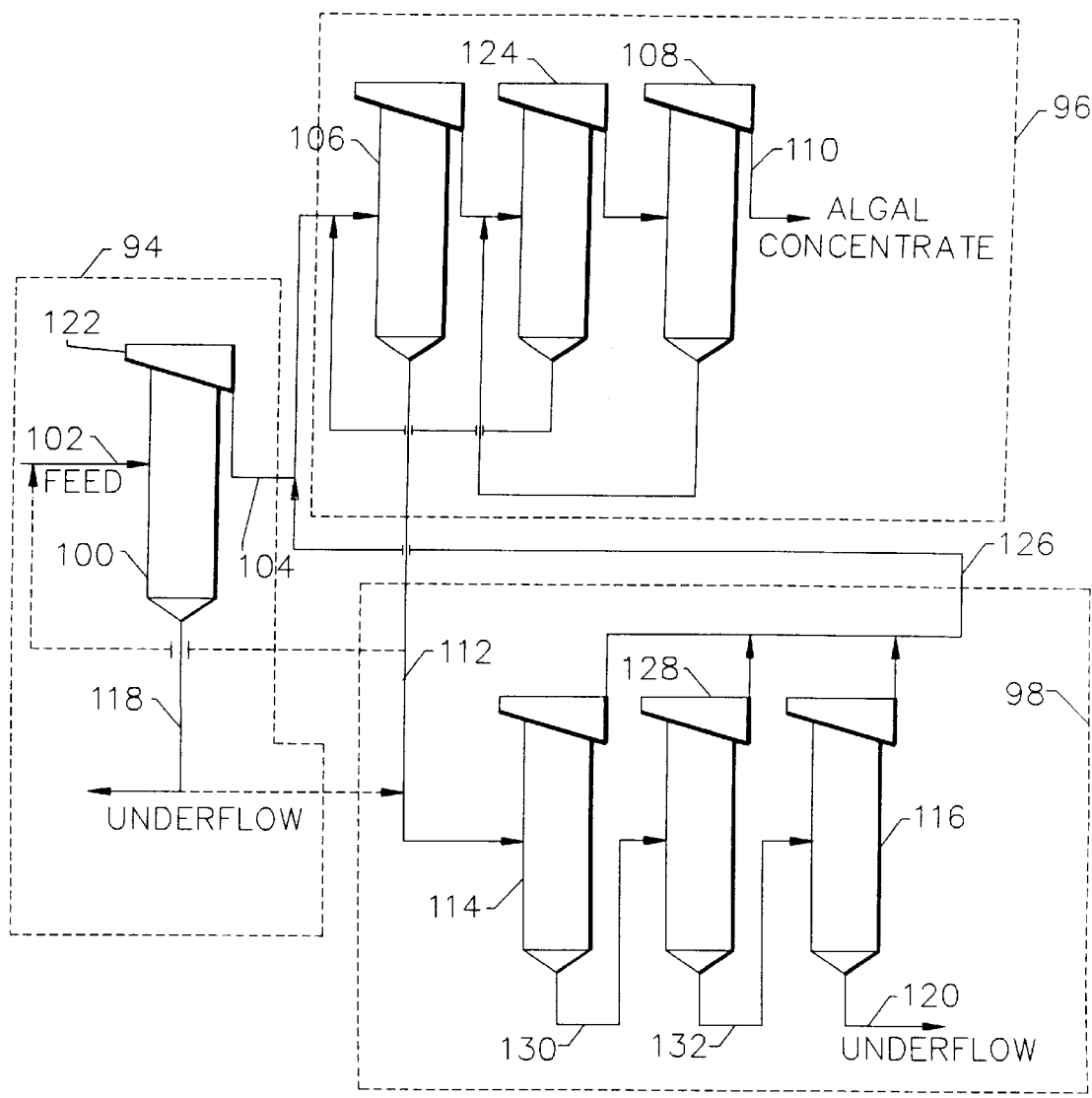
FIG. 6 is a schematic representation of a froth flotation circuit, including roughers, concentrators, and scavengers for dewatering an algal suspension.

A froth flotation circuit is schematically represented in FIG. 6 for froth flotation columns connected in series of the type that may be used in connection with pneumatic froth flotation. However, it should be understood that the principles represented apply to froth flotation circuits generally, including mechanical and pneumatic froth flotation equipment.

The froth flotation circuit represented in FIG. 6 comprises a roughing zone 94, a concentrating zone 96, and a scavenging zone 98. The function of a flotation vessel depends on its location within the circuit in one of the three zones. The algal suspension enters a rougher 100 as a feed stream 102. The overflow from the rougher provides the feed stream 104 to the initial concentrator 106. Algal concentrate is withdrawn from the final concentrator 108 through stream 110. The scavenger feed stream 112 is provided by underflow from the initial concentrator 106 to the initial scavenger 114 to enhance carotenoid recovery. Waste streams of brine depleted in algae are withdrawn as underflow from the rougher 100 and the final scavenger 116 as underflow streams 118 and 120, respectively. As many stages of concentrators and scavengers may be implemented as desired to provide optimum product recovery and concentration. Scavengers can be eliminated, if desired. Alternatively, the underflow from the rougher, which is stream 118, may be provided as the feed stream to the initial scavenger 114 for processing in the scavenging zone 98. In this case, the underflow from initial concentrator 106 may be recycled to the rougher 100, if desired, or withdrawn as a waste stream, or included in the feed to the initial scavenger.

1. Roughing

The rougher 100 functions as the initial froth flotation stage in roughing zone 94 for separating the algae from the brine. The objective of the rougher is to produce high algae recovery with a moderate increase in concentration. Therefore, the rougher typically is operated at conditions that maximize recovery of valuable products with a modest concentration factor. Flotation devices functioning as roughers typically operate at higher superficial gas velocity and thinner froth depth than those functioning as concentrators.

The algal suspension that is pumped as feed 102 to the rougher can be taken from the source in which the algae grow, including a naturally occurring lake or pond, or from some other source, including intensive and extensive ponds. The suspension may be pretreated as needed as previously described to rupture the cells or mechanically filter the brine. Live, intact cells, or ruptured cells, or a combination of each may be provided to the rougher. The rougher should be operated so that a majority of the cells in the feed are ruptured in the rougher if no prior rupture step is performed.

Figure 11:
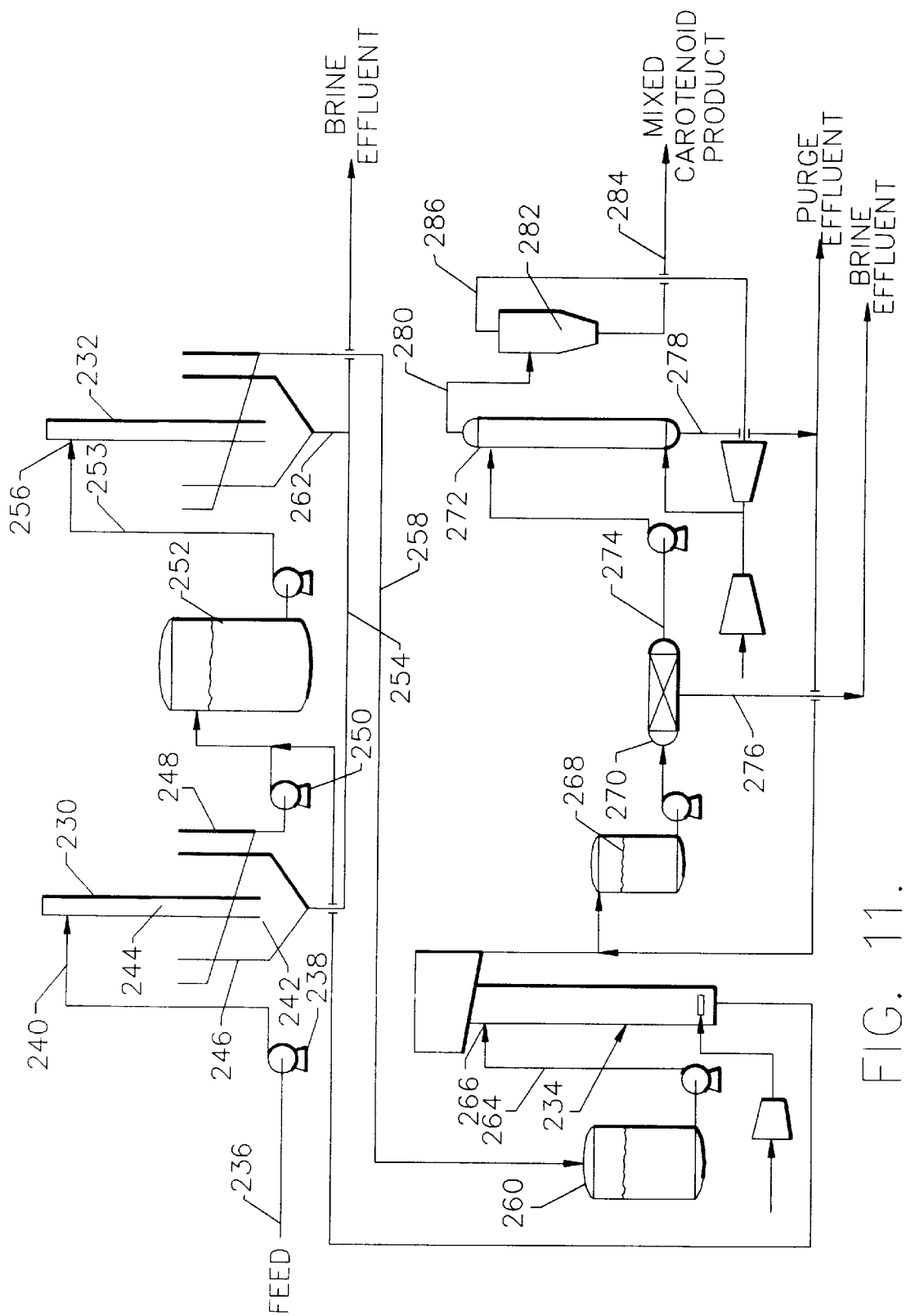
FIG. 11 is a schematic representation of an advantageous froth flotation circuit that includes a Jameson cell rougher, a first Jameson cell concentrator, a second MSTLFLO concentrator, a cross flow microfiltration unit, a continuous dense gas extraction unit, and a cyclone separator for providing a mixed carotenoid product.

The resulting bubble and alga agglomerates float to the surface of the gas and liquid suspension where they collect as a concentrated froth. The concentrate overflows the rougher into a collection launder 122, and then into a holding tank as shown in FIG. 11 at 252. The underflow 118 from the rougher may be recycled to the brine source, discarded, or may be further processed by one or more stages of flotation devices, arranged in parallel.

2. Concentrating

The algal suspension 104 exiting the roughing zone 94 as the overflow from the rougher 100 is further enriched in carotenoids by one or more concentrators 106, 124, and 108 which are shown connected in series. The purpose of the concentrating zone is to produce an algal concentrate enriched in carotenoids for recovery. The algal cells are concentrated in the froth that overflows each concentrator. The overflow from concentrators 106 and 124 provides the feed to the next concentrator. The underflow is typically recycled to the feed for the previous concentrator. Usually, carotenoid concentrations of at least about 2000 ppm are achievable by flotation using the process according to the invention.

The concentrating zone can comprise a single froth flotation vessel or can comprise multiple vessels that receive a feed stream in series or in parallel. The underflow from the concentrators is either discarded, returned to the roughing zone, returned to the previous concentrator, passed to one or more scavengers arranged in series or parallel, or otherwise processed depending on the concentration of carotenoids in the underflow stream.

3. Scavenging

In the scavenging zone 98 carotenoids otherwise lost in the underflow is collected to maximize product recovery. The concentrate 126 from the scavenging zone is recycled to the concentrating zone, and the underflow from the scavenging zone is usually discarded or returned to the brine source. The scavenging zone can comprise a single froth flotation vessel or can comprise multiple vessels that receive a feed stream in series or in parallel.

Shown in FIG. 6 is a scavenging zone 98 that comprises three scavengers 114, 128, and 116 connected in series. Feed to the scavengers is provided as previously described. The underflow streams 130 and 132 from scavengers 114 and 128, respectively, provide feed to the next scavenger in the series. Overflow 126 from each scavenger is supplied to the concentrating zone feed.

D. Mechanical and Pneumatic Flotation Cells in General

Suitable froth flotation devices include the commercially available equipment used for gas and liquid contact. These devices, which are also called "cells", may be classified into two broad groups, mechanical and pneumatic flotation cells. The mechanical flotation cells typically include a rotor and stator mechanism for dispersing the gas and providing efficient bubble and alga contact. The algal bodies rupture in the shear field created by the rotating impeller in a mechanical flotation cell when operated at sufficient speed. There is no need for a separate rupture step if the impeller is operated at sufficient speed.

Pneumatic flotation cells can be most easily distinguished from mechanical flotation cells by the absence of a rotating impeller in the flotation device. In pneumatic flotation cells, bubble and alga collisions are produced by addition of gas only, without any moving parts. Typically there is a need to rupture the algae prior to pneumatic flotation. However, when pneumatic flotation cells are operated under appropriate conditions, as described below, then the algal bodies are ruptured in the cell. Subsequent pneumatic flotation cells, which may operate as concentrators and scavengers, need not be operated at similar conditions because the algal bodies are already ruptured.

Pneumatic and mechanical flotation cells may be used at any or all of the locations in a froth flotation circuit, depending on equipment performance and separation objectives. However, the pneumatic flotation cells typically have advantages over mechanical cells. Higher recovery and throughput may be attained in a pneumatic device as compared to a mechanical device for a given equipment volume and energy input, which usually results in reduced capital and operating costs. Pneumatic devices can be produced from light weight, inexpensive plastics for further cost savings and to promote mobility. These advantages and others are discussed further below.

The mechanical and pneumatic flotation cells described herein have several operating parameters in common, including the gas phase superficial velocity, $J_g$; the gas to feed ratio; the liquid residence time in the flotation device; flotation aid dosage; and the nature of the flotation gas. Several design parameters are also common to various froth flotation devices, including the aspect ratio of the collection zone; the aspect ratio of the separation zone; the method of phase contact, including cocurrent flow, countercurrent flow, crossflow, and mechanical mixing; the method of separating the bubble and alga agglomerates from the pulp; and the method of bubble generation.

Performance of the froth flotation device is quantified in terms of the carotenoid concentration in the froth and carotenoid recovery. There are several geometrical and operating parameters that are specific to each type of froth flotation device, but the major parameters named above are common to the entire field of flotation processes described herein.

1. Mechanical Flotation Cells

Figure 7:
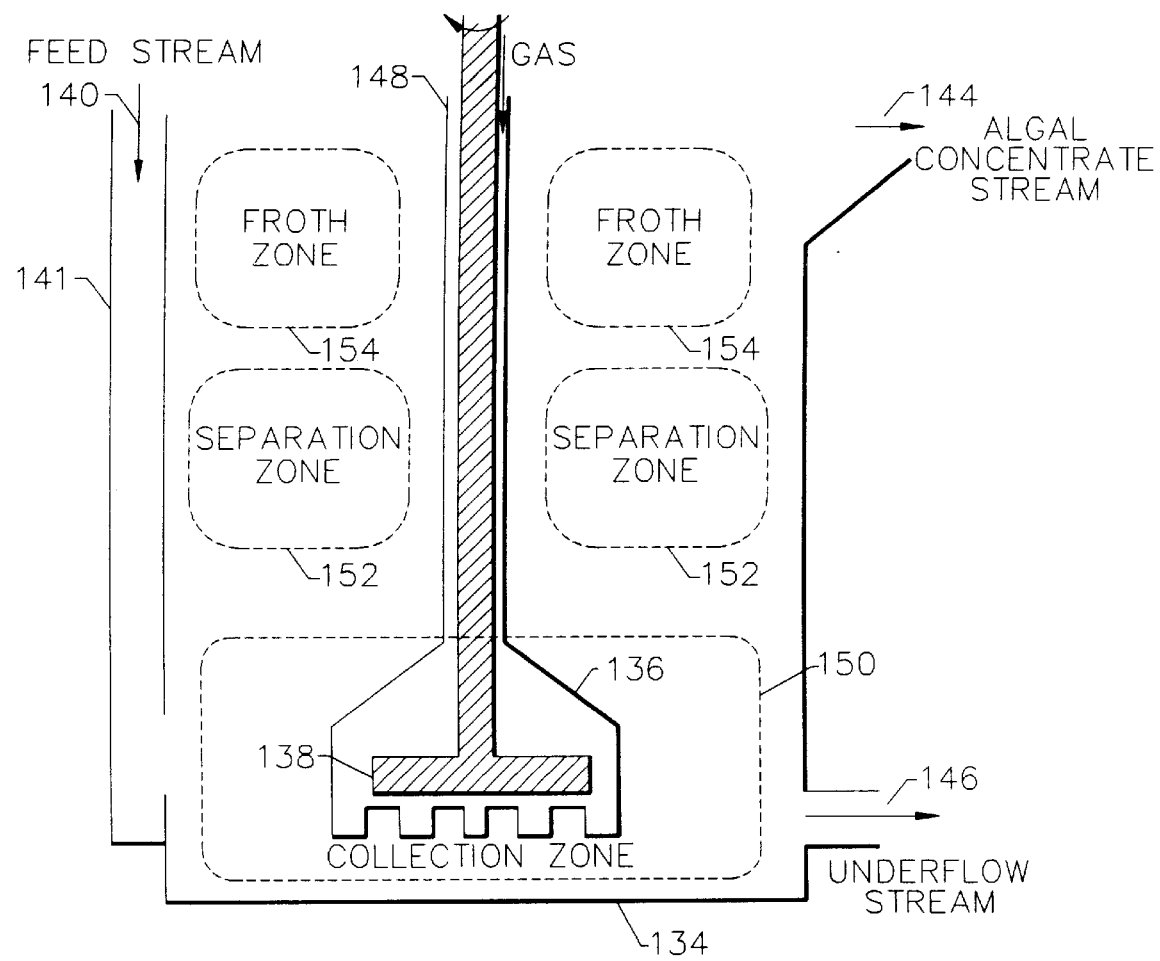
FIG. 7 is a schematic representation of a mechanical froth flotation cell.

The hydrodynamic characteristics of a mechanical flotation cell 134 are illustrated in FIG. 7. Mechanical cells typically employ a rotor and stator mechanism 136 for gas induction, bubble generation, and liquid circulation providing for bubble and alga collision. The ratio of vessel height to diameter, termed the "aspect ratio", usually varies from about 0.7 to 2. Typically, four or more cells 134 similar to that in FIG. 7, each having a centrally mounted rotor and stator mechanism 136, are arranged in series to approach substantially perfect mixing and thereby to minimize liquid phase short circuiting. An auxiliary blower is typically installed to provide sufficient gas flow to the cell.

The collection and separation zones 150 and 152, respectively, are in the same vessel in the mechanical cell. Mechanical cells may be sealed if desired to facilitate operation and recycle with a gas that will not substantially oxidize carotenoids.

The gas is dispersed into fine bubbles by a rotating impeller 138, which serves as the bubble generator. The rotating impeller creates a low pressure zone that induces gas to flow through an aspiration tube 148 into the collection zone 150 where it is dispersed into fine bubbles and mixed with the algal suspension as it is circulated from the bottom of the cell.

The algal suspension enters the mechanical cell as a feed stream 140 through a feed box 141. Bubble and alga contact results from turbulence generated by the rotating impeller. The bubble and alga agglomerates pass out of the collection zone 150 into the separation zone 152, which is relatively quiescent, where they float to the surface and separate from the liquid phase.

The bubble and alga agglomerates are separated from the liquid phase by gravity and collect as a froth concentrated in carotenoids at the top of the cell in froth zone 154. Froth concentrated in carotenoids is withdrawn as an algal concentrate stream 144. The froth normally overflows the cell into a collection launder. Alternatively, the froth may be withdrawn by mechanical means such as a froth paddle. The liquid phase is recirculated to the collection zone and eventually exits the cell as an underflow stream 146 of brine depleted in algae.

The properly designed rotor and stator mechanism entrains the proper amount of gas, disperses it into fine bubbles, and mixes the gas with liquid to accomplish sufficient contact between the algae and the bubbles. Good mixing and sufficient liquid residence time are necessary in the two phase mixing region to provide high bubble and alga collision efficiency, and good flotation performance.

$J_g$ is defined in a mechanical flotation cell as the volumetric gas flow rate divided by the cell cross sectional area parallel to the froth and liquid interface. As the value of $J_g$ increases, the gas holdup increases in the liquid phase and decreases in the froth, resulting in potentially faster flotation kinetics but reduced carotenoid concentration in the froth on a gas free basis. The values of $J_g$ range from about 0.1 to 5 cm/s for recovery of carotenoids from *Dunaliella salina*. Values of from about 2 cm/s to 4 cm/s are somewhat more typical.

The liquid residence time is defined as the volume of the dispersion in the mechanical cell divided by the volumetric liquid flow rate. Longer residence times enable higher recovery of carotenoids in the froth. The residence time ranges from about 3 to 12 minutes for continuous operation for the recovery of carotenoids from *Dunaliella salina*. Residence times greater than 5 minutes are somewhat more typical.

The advantages of a low gas to feed ratio include reduced equipment volume and blower costs in the mechanical cell. The gas to feed ratio ranges from about 5 to 20 for the recovery of carotenoids from *Dunaliella salina*. Gas to feed ratios of from about 5 to 15 are somewhat more typical.

Impeller tip speed influences the bubble size and the recirculation rate through the collection zone. The bubble size decreases and the recirculation rate through the collection zone increases as the tip speed increases. However, higher tip speeds result in greater mechanical wear and power requirements for the impeller drives. The bubble and alga agglomerates may be broken at high tip speeds. Tip speeds range from about 900 to 2500 feet per minute for the recovery of carotenoids from *Dunaliella salina*. Tip speeds of from about 1500 to 1800 feet per minute are somewhat more typical. Tip speeds above about 1500 feet per minute are useful for rupturing the algal bodies.

There are four primary geometrical parameters for mechanical flotation cells. These geometrical parameters are 1) the ratio of rotor submergence to liquid depth, 2) the ratio of tank diameter to impeller diameter, 3) the ratio of liquid depth to tank diameter, and 4) the design of the rotor and stator mechanism. The ratio of rotor submergence to liquid depth ranges from about 0.7 and 0.75 for the recovery of carotenoids from *Dunaliella salina*. The ratio of tank diameter to impeller diameter ranges from about 1.5 to 5.5. A tank diameter to impeller diameter ratio of about 2 is somewhat more frequently used. The ratio of liquid depth to tank diameter ranges from about 0.6 to 0.9. A ratio of liquid depth to tank diameter of from about 0.8 to 0.9 is somewhat more typical.

Rotor and stator mechanisms include those produced by Dorr-Oliver Incorporated of Millford, Conn.; Denver Equipment Company which is a division of Svedala of Colorado Springs, Colo.; Wemco Products of Salt Lake City, Utah; and Outomec Oy of Espoo, Finland.

2. Pneumatic Flotation Cells

Pneumatic flotation cells differ from mechanically agitated cells in several respects. Bubbles are generated by any nonmechanical means known to the art in a pneumatic cell. Bubbles can be produced by a perforated pipe sparger, an orifice plate, a venturi, or a static mixer. A frother solution usually is mixed with the gas when a static mixer is used.

Some pneumatic cells generate finer bubbles than do mechanical cells. Therefore, the collision frequency is potentially higher, and the residence time required for the flotation is generally shorter in a pneumatic cell.

Pneumatic flotation cells, especially columns, usually have a higher aspect ratio than mechanical cells. The ratio of vessel height to diameter typically is greater in the pneumatic cell. It is possible to operate a pneumatic device with a deeper froth bed, allowing for increased drainage time and a drier, more concentrated froth. Wash water can be added to the froth to improve product purity because the vessel height is usually somewhat greater than the vessel diameter.

Another advantage of a pneumatic flotation cell over a mechanical cell is lighter weight and lower costs of materials and construction. The pneumatic flotation vessel can be constructed of inexpensive light weight plastics, and weight and cost are further reduced by the absence of an impeller and drive. Capital and operating costs for the pneumatic flotation cell may be significantly lower than those for the mechanical cells because no mechanical rotor and stator assembly is required for bubble generation and gas and liquid contacting.

Generally speaking, pneumatic flotation cells serving as concentrators may be operated in either the collection limited regime or in the carrying capacity limited regime. In the collection limited regime, the particle collection rate is limited by the number of collisions between bubbles and algae. In the carrying capacity limited regime the bubble surfaces are saturated with algal material. Therefore, the particle collection rate is limited by the rate at which bubble surface area is added to the column. It is advantageous to produce a froth whose surface approaches saturation with algal material because it is desirable to minimize the volume of brine sent to the recovery process.

Referring to FIG. 5, the feed can be either mechanically or chemically treated to render the algae more readily floatable, as desired. The gas is dispersed as fine bubbles by means of a bubble generator in a bubble generation zone. The bubble generator may be either internal or external to the froth flotation device. An example of an internal bubble generator is the perforated pipe sparger. An example of an external bubble generator is a static mixer where the gas is mixed with a frother solution.

The bubbles and the algal suspension feed enter the collection zone where bubble and alga collisions occur to form bubble and alga agglomerates. Bubble and alga collisions may be achieved by countercurrent or cocurrent flow of the gas and liquid phases, or by pneumatic mixing. The agglomerates float through the separation zone to the liquid and froth interface and pass into the froth zone where the gas holdup rapidly increases.

The froth may be contacted with wash water to separate entrained hydrophilic particles and feed water from the algae in the froth. The froth leaves the device enriched in biomass. The liquid passes through the base of the device as an underflow stream depleted of biomass.

Air or an inert flotation gas with recycle may be easily used in pneumatic flotation devices. The gas can be recycled by covering the collection launder. Frother may be added either to the liquid phase or to the gas phase to generate small bubbles.

There are several pneumatic flotation devices available that may be used in accordance with the invention to dewater algae and to recover carotenoids from *Dunaliella salina*. Some of these devices include columns having an aspect ratio greater than one, which provide many of the benefits of the pneumatic devices above discussed. Some of the pneumatic flotation cells and their use in accordance with the invention are described below.

Pneumatic flotation cells include induced gas flotation cells and the air-sparged hydrocyclone, or "ASH". In the induced gas flotation cells, the gas is dispersed in the liquid by passing the liquid and the gas through a nozzle at the bottom of the cell. The ASH utilizes gas transfer through porous walls to create a froth that exits through the overflow.

a. The Jameson Cell

Figure 8:
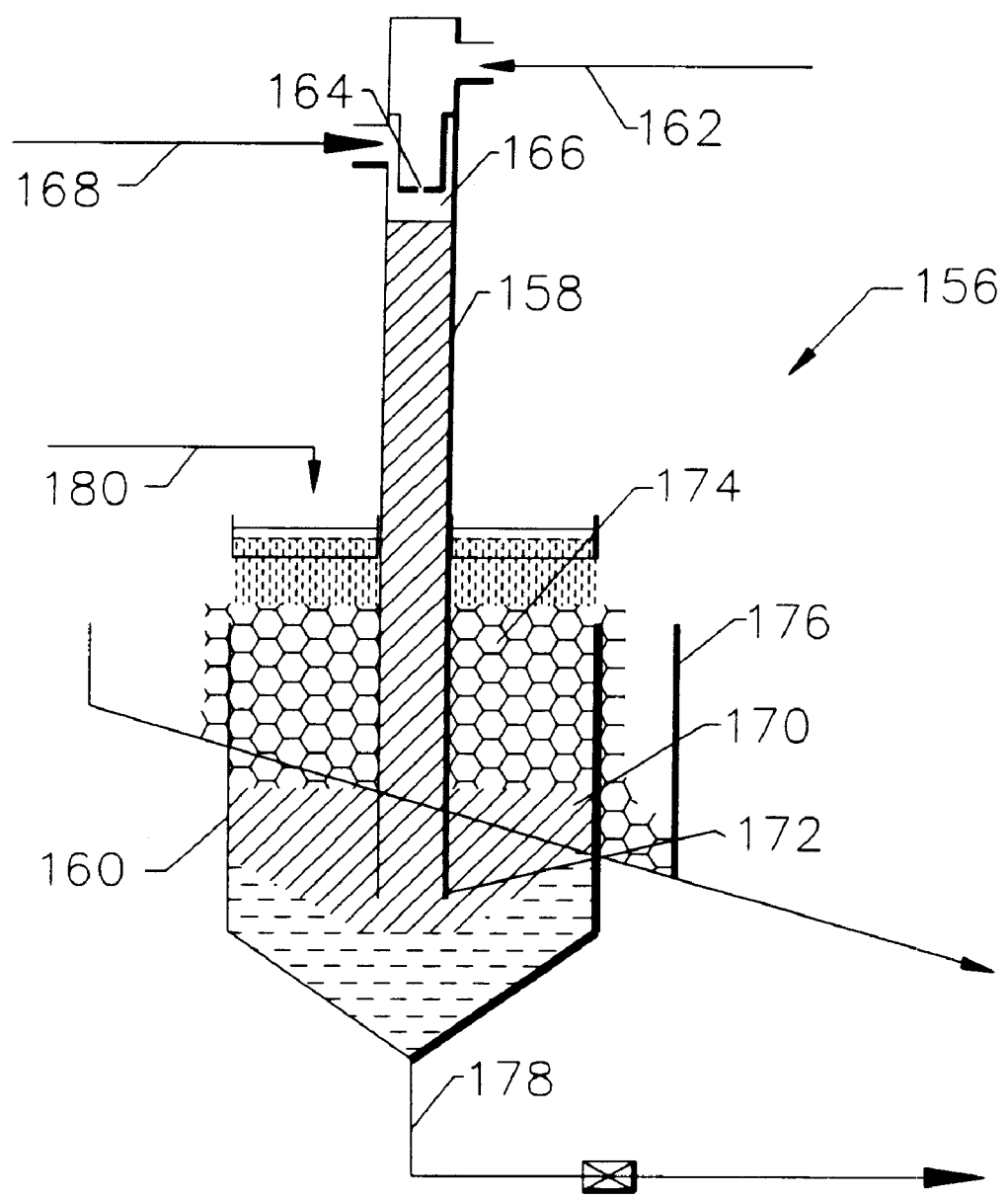
FIG. 8 is a schematic representation of a single downcomer Jameson cell.

A single downcomer Jameson cell 156 is illustrated in FIG. 8. The Jameson cell is described in U.S. Pat. Nos. 5,188,726; 5,332,100; and 4,938,865, the contents of which are incorporated herein by reference in their entirety. For the recovery of carotenoids from *Dunaliella salina* in accordance with the invention, the algal material in the froth produced in the Jameson cell on a gas free basis ranged from about 60 ppm to 13% by weight.

The Jameson cell consists of two primary components. The first component is the downcomer 158, which is a column typically from about 100 to 280 mm in diameter and about 3 m long. The second component is the riser 160. The riser is a tank into which the downcomer empties. The riser typically has a diameter much larger than the downcomer. Alternatively, multiple downcomers may discharge into a single riser.

The downcomer of the Jameson cell defines the collection zone 86 (FIG. 5) and typically has an aspect ratio from about 10 to 30. The riser includes the separation zone 88 (FIG. 5) and the froth zone 90 (FIG. 5), and its aspect ratio is commonly from about 0.5 to 5. The method of phase contact is multiphase cocurrent downward flow in the downcomer. Bubble and alga agglomerates are separated from the brine depleted in algae by gravity in the riser. The bubbles are generated in the downcomer as a result of the entrainment and dispersion of gas in the liquid phase by a high velocity jet.

The algal suspension feed enters the top of the downcomer through line 162 and passes through an orifice plate 164, forming a high velocity liquid jet. Gas is induced into the downcomer headspace 166 through line 168 because the pressure in the headspace of the downcomer is less than atmospheric. The jet impacts the surface of the liquid in the downcomer, which entrains the gas into the liquid phase. The entrained gas is dispersed into fine bubbles by the high velocity gradients generated by momentum dissipation of the jet. The gas and liquid are transported in two phase flow through the downcomer. The two phase flow approaches cocurrent downward plug flow in a vertical pipe, and results in collision of the gas bubbles and algae to form bubble and alga agglomerates. The multiphase dispersion then passes through the base of the downcomer into the riser.

The Jameson cell is operated so that the liquid level 170 in the riser is slightly higher than the end of the downcomer 172 to maintain a liquid seal. The bubble and alga agglomerates separate from the brine in the riser. The agglomerates float to the surface of the riser where they are collected as a froth 174 that overflows the cell into a collection launder 176. The brine depleted in algae underflows the cell as stream 178.

The riser may be as deep as required to optimize product recovery and concentration in the froth. The riser may need to be deeper to avoid entrainment of agglomerates in the underflow stream 178 for very fine bubbles having a diameter of less than about 500 microns. Froth depth may be as low as 50 millimeters for high recovery operations, but typical values range from 300 to 800 millimeters. Wash water 180 may be added to the froth to improve concentrate purity. The Jameson cell can be operated with air or can be enclosed and operated with a gas that minimizes carotenoid degradation.

Typically the operating conditions in a Jameson cell, particularly riser superficial gas velocity, $J_g$, vary depending on the type of service required, either roughing, scavenging, or cleaning.

The $J_g$ in a Jameson cell is defined as the superficial gas velocity in the riser, and is equal to the volumetric gas rate divided by the riser cross sectional area parallel to the froth and liquid interface. The cell $J_g$ is selected to provide adequate separation of bubble and alga agglomerates in the riser and to ensure froth stability. The maximum value of $J_g$ is at the point of froth flooding, where the gas holdup values in the separation zone and in the froth zone are equal, resulting in a loss of interface. Significant entrainment of bubble and alga agglomerates into the underflow stream 178, representing a recovery loss, may occur at higher $J_g$ values before the cell floods. The minimum value of $J_g$ is dictated by the requirement to produce a stable froth. If the gas rate is too low, the froth may collapse, resulting in significant reentrainment of agglomerates into the separation zone in the riser 160.

Riser superficial gas velocity depends on system properties and the type of service selected. The value of $J_g$ ranges from about 0.1 to 1.0 cm/sec for dewatering *Dunaliella salina* in rougher service. Values of $J_g$ in a rougher of from about 0.3 to 0.5 cm/sec are somewhat more typical. The value of $J_g$ ranges from about 0.05 to 0.5 cm/sec for dewatering *Dunaliella salina* in concentrator service. Values of $J_g$ in a concentrator of from about 0.1 to 0.35 cm/sec are somewhat more typical.

It is believed that the relatively low superficial gas velocity is due at least in part to the presence of surface active agents in the algae. High concentrations of surface active agents may induce froth flooding at lower values of $J_g$. It is surprising that such low $J_g$ values are required for the flotation of carotenoids. It is even more surprising that the frothers naturally occurring in the algae are of sufficient concentration and surfactant power to facilitate flotation of the carotenoids, even in brines saturated with sodium chloride.

The downcomer superficial velocity in the Jameson cell is computed from the feed flow rate and the cross sectional area of the downcomer. The downcomer residence time is a closely related parameter, and is defined as the volume of the downcomer divided by the volumetric feed rate. The values of these two parameters directly impact the equipment throughput and performance. A long residence time, which also means a low superficial velocity, promotes a high algae collection efficiency, and therefore high recovery of carotenoids in the froth. A short residence time and high superficial velocity increases column throughput.

Downcomer superficial velocity ranges from about 0.1 to 0.4 m/s for recovery of carotenoids from *Dunaliella salina*. Downcomer residence time varies from about 9 to 30 s. Values for downcomer superficial velocity and residence time for recovery of carotenoids from *Dunaliella salina* in Jameson cells in rougher and scavenger service typically are from about 0.15 to 0.3 m/s and from 10 to 20 s, respectively. Values of downcomer superficial velocity and residence time are from about 0.1 to 0.2 m/s and from 15 to 25 s, respectively, for Jameson cells in concentrator service.

The gas to feed ratio is defined as the ratio of the gas volumetric flow rate to the liquid volumetric flow rate. Decreasing the gas to feed ratio in the Jameson cell results in a stabilizing effect on the column because of the formation of finer bubbles having a more uniform size distribution. As the gas to feed ratio is increased, coarser bubbles having a smaller specific surface and broader size distribution are produced. Eventually, large bubbles are formed which rise against the downward flow.

For recovery of carotenoids from *Dunaliella salina*, the gas to feed ratio ranges from about 0.3 to 0.9 for rougher, scavenger, and concentrator service in Jameson cells. Gas to feed ratios are somewhat more typically from about 0.4 to 0.7 for both applications.

The feed pressure at the downcomer inlet determines the velocity of the jet. Feed pressure varies from about 20 to 60 psig for recovery of carotenoids from *Dunaliella salina* where mechanical pretreatment was applied to rupture the algae and render them more floatable. Values somewhat more typically range from about 50 to 60 psig for rougher and scavenger service and from about 20 to 25 psig for concentrator service.

Jet velocity ranges from about 8 to 25 m/s for rougher, scavenger, and concentrator service for recovery of carotenoids from *Dunaliella salina*. Values are somewhat more typical that range from about 10 to 20 m/s for rougher and scavenger service and from about 8 to 15 m/s for concentrator service.

Two design ratios for the Jameson cell are the downcomer diameter to orifice diameter ratio and the riser diameter to downcomer diameter ratio. The downcomer to orifice diameter ratio ranges from about 7 to 13 for recovery of carotenoids from *Dunaliella salina*. Values of from about 8 to 10 are somewhat more typical. The riser to downcomer diameter ratio varies from about 2 to 10 for recovery of carotenoids from *Dunaliella salina*. Values greater than about 5 are more typical.

It is also possible to operate the Jameson cell at higher feed pressures to eliminate the need for a separate rupture step. Operating the Jameson cell at high feed pressures to rupture the algae in the orifice obviates any need for a mechanical or chemical pretreatment step to render the algae more floatable. The high pressure range may be defined as feed pressures greater than 60 psig. Typically, the Jameson cell is operated at a feed pressure of from about 150 to 300 psig to rupture the cells.

The Jameson cell can be operated at feed pressures greater than 60 psig by installing a smaller orifice plate in the nozzle than is typically used. However, a high jet velocity usually generates bubbles too fine to separate in the riser, resulting in the entrainment of bubble and alga agglomerates in the underflow stream 178 (FIG. 8). It may be necessary to install a divergent spray nozzle or a baffle to deflect the downward momentum of the jet when operating at these high feed pressures.

The velocity of the jet passing through the orifice at the top of the downcomer may be calculated from the Bernoulli equation. The jet consists of three regions: the free jet, the plunging jet, and the mixing region. The feed is in the form of a free jet when the feed passes through the orifice plate into the downcomer. The free jet creates a low pressure region in the headspace and transports gas to the jet surface. The region where the jet impacts the surface of the liquid is called the plunging jet, and is where gas is entrained into the liquid. In the mixing zone below the surface of the liquid, the momentum of the jet is dissipated. The resulting high velocity gradients break up the entrained gas into small bubbles.

b. Multistage Loop-Flow Flotation (MSTLFLO) Column

Figure 9:
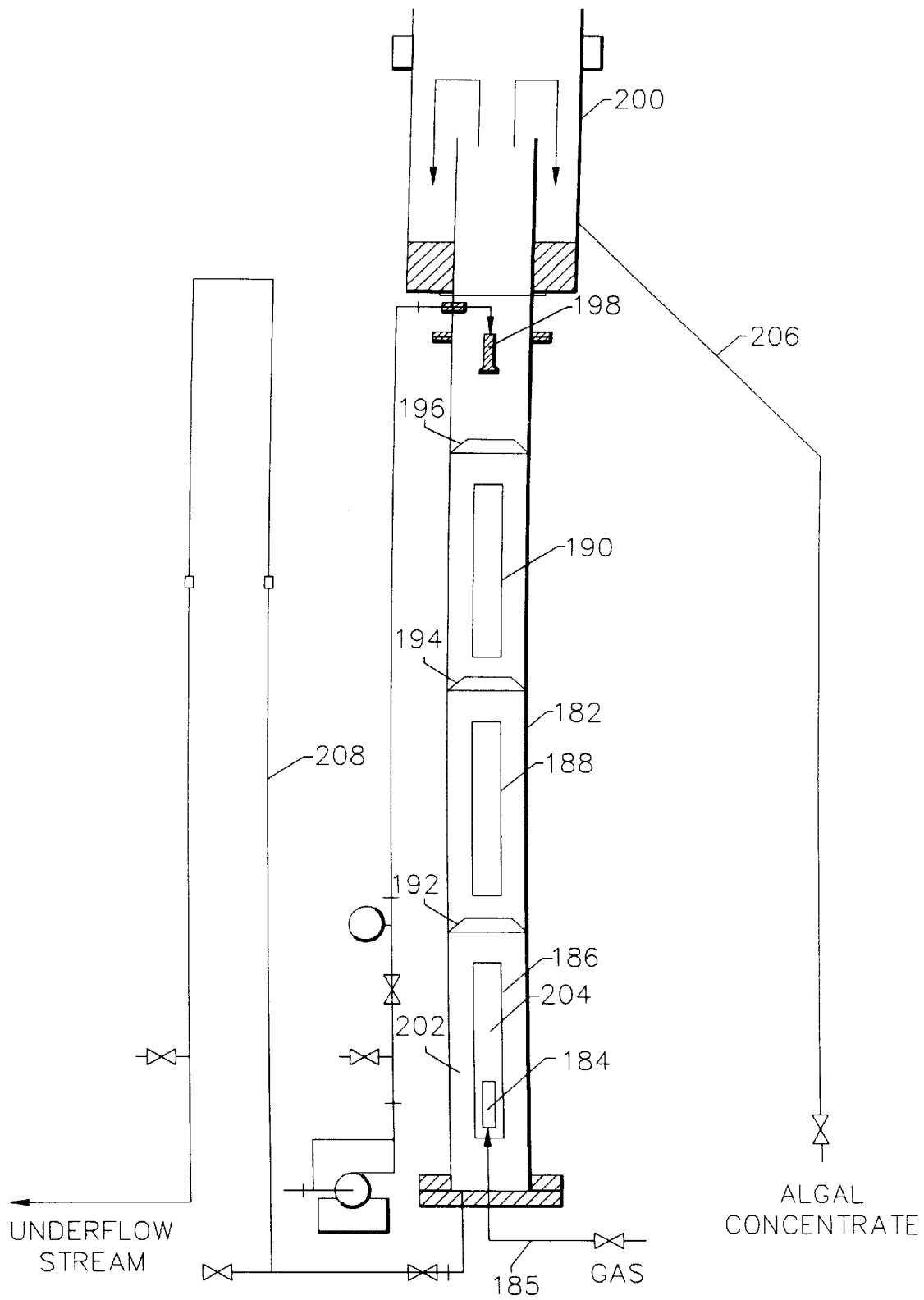
FIG. 9 is a schematic representation of a multi-stage loop flow froth flotation column, which is also called a MSTL-FLO column.

A multistage loop-flow froth flotation column 182 is represented in FIG. 9. The MSTLFLO is a modified bubble column consisting of: a sparger 184 for introducing gas into the base of the column; a series of vertical baffles, draft tubes 186, 188, and 190 that are mounted in the column; baffles 192, 194, and 196 at the top of the draft tubes 186, 188, and 190, respectively, to generate proper hydrodynamics; a feed distributor 198; and a collection launder 200 that is also mounted concentrically with respect to the column. The MSTLFLO column is described by D. X. He, F. X. Ding, H. Hu, and S. H. Chiang in a 1995 article entitled "A Multiple-loop Flotation Column for Wastewater Treatment" at pages 133 through 138 in volume 5 of *Separations Technology*. The He et al. article is incorporated herein in its entirety by reference.

Figure 10:
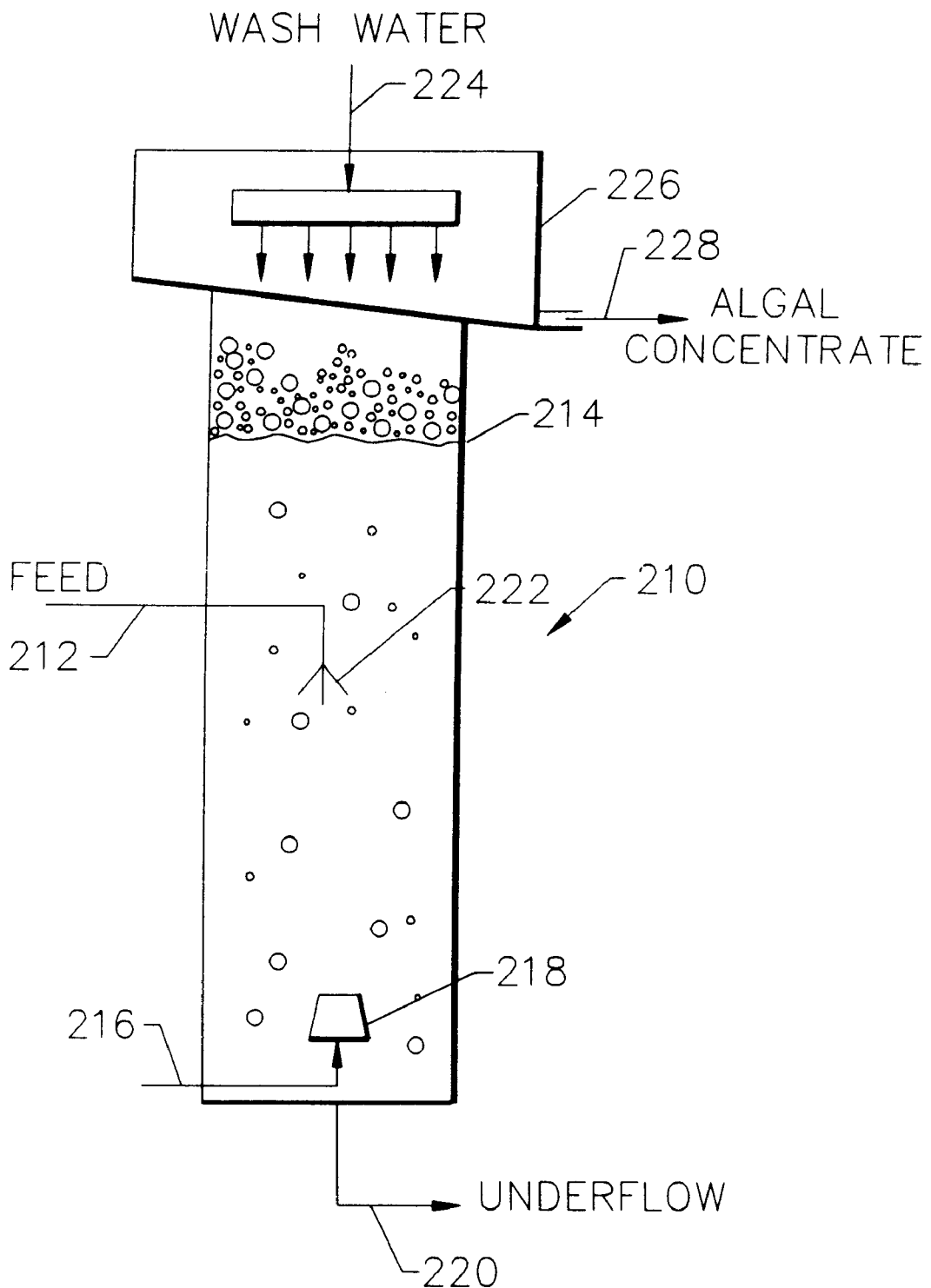
FIG. 10 is a schematic representation of a Canadian column, which is sometimes also called a bubble or conventional column.

A primary design feature of the MSTLFLO column is the arrangement of multiple stages of draft tubes. Gas from line 185 is sparged inside the draft tube 186 at the bottom of the column and results in a higher gas holdup inside the draft tube than in the annular region 202 between the draft tube and the column wall. The difference in gas holdup creates a circulation pattern. The gas and liquid dispersion flows upward in the region 204 inside the draft tube, which functions as a riser, and downward in the annular region 202, which functions as a downcomer. The flow in the downcomer approaches multiphase cocurrent downward plug flow. A more uniform bubble size distribution results from the loop flow hydrodynamics that reduces axial mixing. Flotation kinetics of the MSTLFLO column are improved compared to a conventional bubble flotation column, also called a Canadian column, which does not include draft tubes. A bubble column is represented in FIG. 10. The MSTLFLO column may be transformed into a bubble column by removal of the draft tubes.

The collection and separation zones 86 and 88, respectively, (FIG. 5) are in the same vessel of the MSTLFLO column. The vessel has an aspect ratio greater than 5. While not wishing to be bound by theory, the collection zone in the MSTLFLO column may be considered to be the downcomer and riser of each draft tube in which there is multiphase cocurrent plug flow. The separation zone for the column is above the feed distributor 198 and below the gas liquid interface. The agglomerates collect in the froth zone above the froth and liquid interface and overflow the column into collection launder 200. The froth collapses to form a concentrated algal suspension that is removed through line 206. An underflow stream of brine depleted in algae is taken from the bottom of the column through line 208.

The superficial gas velocity, $J_g$, in the MSTLFLO column is defined as the volumetric gas flow rate divided by the column cross sectional area. As $J_g$ increases, the gas holdup in the multiphase dispersion increases, resulting in higher algae collection efficiency. However, the gas holdup in the froth decreases with increasing $J_g$ because the rising bubbles entrain more water into the froth. As the maximum value of $J_g$ is approached, the gas holdup in the froth and in the gas and liquid dispersion become equal, resulting in column flooding and loss of interface.

$J_g$ values range from about 0.1 to 1.0 cm/s for the recovery of carotenoids from *Dunaliella salina*. Values of from about 0.2 to 0.5 cm/s are somewhat more typical. It is surprising that such low $J_g$ values are required for the flotation of carotenoids. It is even more surprising that the frothers naturally occurring in the algae are of sufficient concentration and surfactant power to facilitate flotation of the carotenoids, even in brines saturated with sodium chloride and in the presence of other ions.

The liquid residence time is defined as the volume of the MSTLFLO column divided by the volumetric liquid feed rate. A long residence time enables high recovery of carotenoids in the froth. A short residence time increases column throughput. In the collection limited regime, liquid residence times range from about 2 to 20 minutes for recovery of carotenoids from *Dunaliella salina*. In the carrying capacity limited regime the residence time is greater than 20 minutes.

In the MSTLFLO column the advantages of using a low gas to feed ratio include reduced equipment volume and gas compression costs. The gas to feed ratio ranges from about 0.10 to 1.5 for the recovery of carotenoids from *Dunaliella salina*. Values of from about 0.2 to 0.8 are somewhat more typical. Such low gas to feed ratios are surprising and advantageous for the flotation of carotenoids.

It may be advantageous to operate the MSTLFLO column in an inert atmosphere of carbon dioxides, nitrogen, helium, or noble gas to minimize oxidation of carotenoids. Use of carbon dioxide may improve flotation kinetics compared to air.

Multiple stages of draft tubes are used to reduce the axial mixing in the column and minimize short circuiting, thus improving performance of the column. The number of stages ranges from about 1 to 5 for recovery of carotenoids from *Dunaiella salina*. More than one should ordinarily be used.

The value of the ratio of the draft tube diameter to the column diameter utilized for the recovery of carotenoids from *Dunaliella salina* ranges from about 0.5 to 0.9. Values of from about 0.5 to 0.7 are somewhat more typical in carotenoid recovery from *Dunaliella salina*.

A relatively stable froth results from the flotation of carotenoids from *Dunaliella salina*. A launder with a relatively large cross sectional area is required to accommodate the froth. A ratio of launder diameter to column diameter of 2 was used for recovery of carotenoids from *Dunaliella salina*. This ratio should normally be greater than 1.25.

c. Canadian Column

The Canadian column, also called the conventional or bubble column, is represented in FIG. 10. The bubble column 210 typically is about 0.5 to 3.0 meters in diameter and about 9 to 15 meters tall. The cross section may be either square or circular.

The algal suspension feed enters the column through line 212 about 1 to 2 meters below the froth and liquid interface 214 and flows downward. The gas enters the base of the column through line 216 and is dispersed into fine bubbles, typically by means of a sparger 218. An inert gas, including carbon dioxide, nitrogen, helium, or a noble gas may be used to minimize carotenoid degradation. The gas, typically air, may be injected directly into the base of the column as an internal sparge as shown at 218, or it may be first contacted with water, algal suspension, frother solution, or a combination thereof, before injection as an external sparge. Internal spargers typically are fabricated from perforated pipe covered with fabric, such as filter cloth, or from perforated rubber.

The countercurrent flow of gas and algal suspension results in bubble and alga collision in the collection zone 86 (FIG. 5), which is defined as the region below the feed distributor 222 (FIG. 10). The separation zone for the column is above the feed distributor 222 and below the froth and liquid interface 214. The agglomerates collect in the froth zone above the froth and liquid interface and overflow the column into the collection launder 226. The froth collapses to form a concentrated algal suspension that is removed is removed through line 228. The brine, depleted of algae, underflows the column as stream 220.

The column may be operated at any desired froth depth, although in practice froth depths ranging from 50 to 100 cm typically are used. Wash water may be added to the froth as shown at 224 to separate entrained hydrophilic particles from the algal biomass. To maximize cleaning efficiency, the column is typically operated with positive bias, which means that there is a net flow downward of water through the froth. The bias water leaves the column through the underflow stream. The underflow stream flow rate should be greater than the feed rate to maintain the froth and liquid interface level.

d. Air Sparged Hydrocyclone (ASH)

For the recovery of carotenoids from *Dunaliella salina* in accordance with the invention, the algae concentration in the froth on a gas free basis ranged from about 0.001% to 0.3% by weight for the ASH unit. The ASH consists of a tangential feed inlet to a cylindrical hydrocyclone having a porous wall through which compressed gas enters the unit. A sloped froth pedestal is located at base of the cyclone so that the underflow cross sectional area can be easily varied. Various diameter vortex finders may be used to control the froth takeoff rate.

Feed enters the ASH unit tangentially at the top of the cyclone and follows a helical path before exiting at the base through the annular underflow opening. Bubbles are generated by passing air through the porous wall. Collisions between the algae and bubbles occur in the outer vortex, which defines the collection zone 86 (FIG. 5). The gas and liquid phases are contacted in a cross flow pattern as the liquid moves toward the base of the hydrocyclone. Centrifugal force is used to separate the bubble and alga agglomerates from the brine depleted in algae in the separation zone 88 (FIG. 5), which can be considered to be the undefined boundary between the inner and outer vortexes. Bubble and alga agglomerates are transported to the froth zone 90 (FIG. 5), which forms the inner vortex that moves up to exit the top of the cyclone.

$J_g$ is defined for an ASH unit as the volumetric gas flow rate through the membrane divided by the cross sectional area of the membrane. The values of $J_g$ range from about 0.7 to 6 cm/s for the recovery of carotenoids from *Dunaliella salina*. Values greater than about 3 cm/s are somewhat more typical.

The liquid residence time for the ASH unit is defined as the volume of the ASH unit divided by the liquid volumetric flow rate. The residence time ranges from about 1 to 10 seconds for the recovery of carotenoids from *Dunaliella salina*.

The gas to feed ratio ranges from about 0.4 to 6 for the recovery of carotenoids from *Dunaliella salina*. Values greater than 3 are somewhat more typical.

e. EKOFLOT Pneumatic Flotation Cell

The algal feed suspension 80 (FIG. 5), is pumped to the top of the column through a venturi device which functions as the bubble generation zone 84 (FIG. 5). Gas is entrained into the algal suspension and the resulting mixture passes down through the feed pipe, where most of the bubble and alga collisions occur. This feed pipe serves as the collection zone 86 (FIG. 5). The liquid and gas dispersion containing the bubble and alga agglomerates flows through a distributor into the separation zone 88 (FIG. 5), which is in a separate vessel. The agglomerates float to the surface where they accumulate in a froth zone 90 (FIG. 5). The brine depleted in algae underflows the vessel as stream 92 (FIG. 5).

The froth crowder, an inverted cone, may be raised or lowered to vary the size of the froth area to optimize the separation. The froth may be contacted with wash water to improve product purity. The cleaned froth overflows the vessel into a collection launder where it is removed as a concentrate. The residence time in the separation zone ranges from two to three minutes, which is comparable to the Jameson cell. However, the residence time in the downcomer of the Jameson cell is usually from about 5 to 10 seconds. The residence time in the aerator device of the EKOFLOT vessel is on the order of milliseconds. The aerator device of the EKOFLOT cell is where the bubble and alga collisions occur, which defines the collection zone.

f. Microcel™ Microbubble Flotation Column

The Microcel™ column is described in U.S. Pat. Nos. 4,981,582 and 5,167,798, the contents of which are incorporated herein by reference in their entirety. The Microcel™ column is manufactured by ICF Kaiser Engineers, Inc., which is located in Pittsburgh, Pa. The column consists of an aeration zone at the base of the column, a one way plate above the aeration zone which allows microbubbles to rise into the liquid but prevents solids from settling into the aeration zone, a collection zone, and a froth zone. The feed algal suspension 80 (FIG. 5) enters the column below the froth and liquid interface and flows downward. The gas 82 (FIG. 5) is dispersed in liquid outside of the column by means of a microbubble generator, which functions as the bubble generation zone 84 (FIG. 5). Suitable liquids include the algal suspension feed 80, the underflow stream 92, a frother solution, or combinations thereof. Micro bubbles are generated by this external sparger that range in size from 50 to 400 microns. The micro bubbles are then introduced into the aeration zone.

The liquid used to generate the microbubbles exits the aeration zone depleted in bubbles through a port and typically is recycled to the microbubble generator. The microbubbles leave the aeration zone through the one way plate, where they enter the collection zone 86 (FIG. 5) which is the region below the feed distributor and above the aeration zone. Because of the small size of the bubbles, the flow in the collection zone is substantially quiescent, resulting in efficient countercurrent contact of the algal suspension and the microbubbles. The brine, depleted in algae, leaves through a port in the one way plate as an underflow stream. The bubble and alga agglomerates rise through the collection zone where they accumulate in the froth zone. Wash water may be added to the froth to separate entrained hydrophilic particles from the algal biomass. The froth, enriched in carotenoids, overflows the column into a collection launder where it is removed as a concentrate.

The microbubble generator consists of a series of small fins placed such that the fluid direction changes frequently. The design is similar to that of a static mixer. The liquid is pumped at a rather high velocity through the mixer while the desired volume of gas is metered into the liquid line prior to entering the mixer. The fluid shear disperses the gas into microbubbles. Microbubble suspensions containing greater than 50 percent gas on a volume basis may be generated using this technique.

g. Other Flotation Devices

The principles of the invention apply to flotation devices too numerous to mention other than the specific mechanical and pneumatic flotation devices discussed above. These other devices differ from those discussed above only in detail primarily in that they have a different geometry or employ different means of bubble and algal contact, phase separation, or bubble generation.

Whatever combination of adsorptive bubble separation techniques, deep bed filtration, and microfiltration is chosen, the algal suspension should be concentrated to a level that provides the most attractive process, taking into account a number of factors, including the economies involved. Extraction of components from less concentrated algal suspensions may be impractical because of the large size of vessels needed for contacting the suspension with solvent or because of the quantities of solvent needed. Deep bed filtration, adsorptive bubble separation, and microfiltration can be used in combination, separately, or in combination with other techniques for dewatering algal suspensions to achieve the desired concentration and economies for extraction.

E. Advantageous Froth Flotation Circuit

One objective of using adsorptive bubble separation processes for the recovery of carotenoids, especially froth flotation processes, is to produce a froth with the highest concentration of carotenoids possible. Any froth flotation device could be used at any location in the flotation circuit. However, the froth flotation methods discussed above are not necessarily equivalent in their ability to concentrate carotenoids in a froth. One advantageous froth flotation circuit for dewatering algae, including *Dunaliella salina*, is described below with reference to FIG. 11. Jameson cells are used as the rougher 230 and the first concentrator 232. A MSTLFLO column is used as a second concentrator 234, which is connected in series to the Jameson cell concentrator 232. The Jameson cells and the MSTLFLO column can be mounted on a raft, trailer, or other mobile device as previously described to facilitate obtaining the algal feed stream.

As shown in FIG. 11, a feed stream 236 of *Dunaliella salina* in brine is obtained from a source thereof. The source can comprise a naturally occurring source, including The Great Salt Lake in Utah or an extensive or intensive pond. The feed stream may be obtained by using a centrifugal pump as previously described, which may be a mobile floating pump. The feed is pumped through a pump 238 to the feed entrance 240 of Jameson cell rougher 230.

The algae are ruptured in a pump loop or by another mechanism as previously described prior to the feed entering the Jameson cell rougher.

The froth is collected in a collection launder 248 and is either collapsed and pumped conventionally or pumped through a froth pump 250 to a storage tank 252 and stored as a carotenoid enriched feed 253 for the Jameson cell concentrator 232. The underflow stream 254 can be disposed of or returned to the source or otherwise treated as described above in connection with the more general discussion of flotation circuits at V. C.

The carotenoid enriched feed 253 to the Jameson cell concentrator is pumped to the feed inlet 256 and separated in the Jameson cell. A drier froth typically is produced compared to the rougher 230. The enriched carotenoid stream 258 is stored in a feed tank 260 for the MSTLFLO column concentrator 234. The underflow stream 262 is treated similarly to the underflow stream of the rougher.

The carotenoid enriched feed stream 264 is pumped from the storage tank 260 to the feed inlet 266 for the MSTLFLO concentrator column 234 and separated therein as previously described. A still drier froth is produced that is further enriched in carotenoids and is collected and stored in a storage tank 268 for further treatment. Further treatment can include microfiltration to further dewater the algae as discussed above or extraction by any of the methods discussed below.

A microfilter 270, as described above, followed by a dense gas extraction unit 272 is shown in FIG. 11. Microfiltration increases the concentration of carotenoids by an order of magnitude over the froth flotation circuit, to about 20,000 ppm in retentate stream 274, which is suitable for dense gas extraction. The permeate stream 276 is a waste brine solution that can be discarded or returned to the lake or pond from which the feed stream was obtained, depending on the chemical additives, if any, present in the-waste brine.

The retentate stream 274 is pumped as a feed stream to a dense gas extraction unit 272. The dense gas, which is carbon dioxide in the present case, is fed in counter current flow to the feed stream in a manner that is believed to be well known to the skilled artisan and is further discussed below in connection with dense gas extraction. The underflow 278 from the dense gas extraction unit, which is the raffinate, is a carotenoid depleted waste stream that can be discarded or further treated as discussed below at VI in connection with extraction of products from the cell mass after carotenoids have been removed.

The extract 280 from the dense gas extraction unit overflows the column and is expanded into a separator 282 to separate the mixed carotenoids product from the dense gas. The mixed carotenoids exit the separator as the underflow stream 284. The dense gas 286 exits the separator overhead and is recycled through a compressor to the base of the dense gas extraction unit. The mixed carotenoids product can be further processed as discussed below to recover specific carotenoids.

VI. Recovering Selected Components from Concentrated Algal Suspensions

Returning to FIG. 1, steps 30 and 32, the carotenoids may be recovered from the concentrated algal suspension by any of several extraction processes employing a variety of solvents. Extraction processes can be selected from among liquid/liquid extraction, solid/liquid extraction, which is also called leaching, liquid/liquid/solid extraction, which is a ternary phase extraction in which two immiscible phases are formed in the presence of a solid material, and dense gas extraction, as described above.

Any organic solvents that are immiscible with water at a concentration greater than about 100 ppm should be useful for extraction of carotenoids from a suspension of *Dunaliella salina* in brine. The organic solvent should be one that at least does not adversely change the physical and chemical characteristics of carotenoids. Solvents can be selected from synthetic and natural flavorants, edible oils, petrochemicals, dense gases, and combinations of these so long as a system results having two or more immiscible phases. However, some of these solvents are more desirable than others for various reasons as discussed below and the results obtained are not necessarily equivalent.

Petrochemical solvents typically are of low viscosity, and the solute molecular diffusivity is favorable. Carotenoids typically are highly soluble in petrochemical solvents and concentrated extracts are possible. Petrochemical solvents include: the aliphatic hydrocarbons, such as hexane, pentane, octane, petroleum ether, cyclohexane, methylene chloride, methanol, ethanol, and other low boiling alcohols; aromatics including benzene and toluene; and numerous other petrochemicals not listed. Combinations of petrochemical solvents may be used if desired.

However, it should be recognized that petrochemical solvents generally are not considered desirable as solvents for extraction of carotenoids for the preparation of nutritional supplements. Solvent residues are normally removable at least to some extent by chromatography. Nevertheless, the use of compounds derived from petroleum to process nutritional supplements and the presence of any petroleum residue in a nutritional supplement is objectionable to many people.

Edible oils are preferred to petrochemical solvents from a nutritional standpoint. Edible oils may be obtained from plant or animal sources, including fish oils. Edible vegetable oil solvents include corn, olive, soybean, safflower, sunflower, and numerous other oils. Combinations of edible oils may be used, if desired.

However, compared to petrochemical solvents, edible oils typically are more viscous, and the solute molecular diffusivity is lower. Carotenoids normally have limited solubility in edible oils and concentrated extracts are difficult to obtain without steps that could change the chemical and physical characteristics of the carotenoids, including applying excessive heat.

Synthetic and natural flavorants typically are more desirable than petrochemical solvents and edible oils. Naturally derived flavorants have appeal in nutritional supplements. Flavorants classified by the Flavor and Extract Manufacturers Association, or FEMA, as Generally Recognized As Safe, or GRAS, do not have the drawbacks of petrochemical solvents in association with nutritional supplements. The presence of residual flavorant solvents in nutritional supplements is generally acceptable in comparison with petrochemical solvents, which reduces downstream purification and recovery costs. Flavorants can be selected to have boiling points, viscosities, and molecular diffusivity properties comparable to petrochemical solvents.

Examples of flavorants that are suitable for this invention include methyl-, ethyl-, propyl-, butyl-, isobutyl-, benzyl-, and octyl- esters with the carboxylic acid component of the ester including acetate, ethanoate, propionate, butyrate, hexanoate, caproate, heptanoate, octanoate, decanoate, cinnamate, and isovalerate. Other examples of flavorants include, but are not limited to, benzaldehyde, other aldehydes, limonene, and other terpenes. Combinations of flavorants may be used, if desired.

Figure 12:
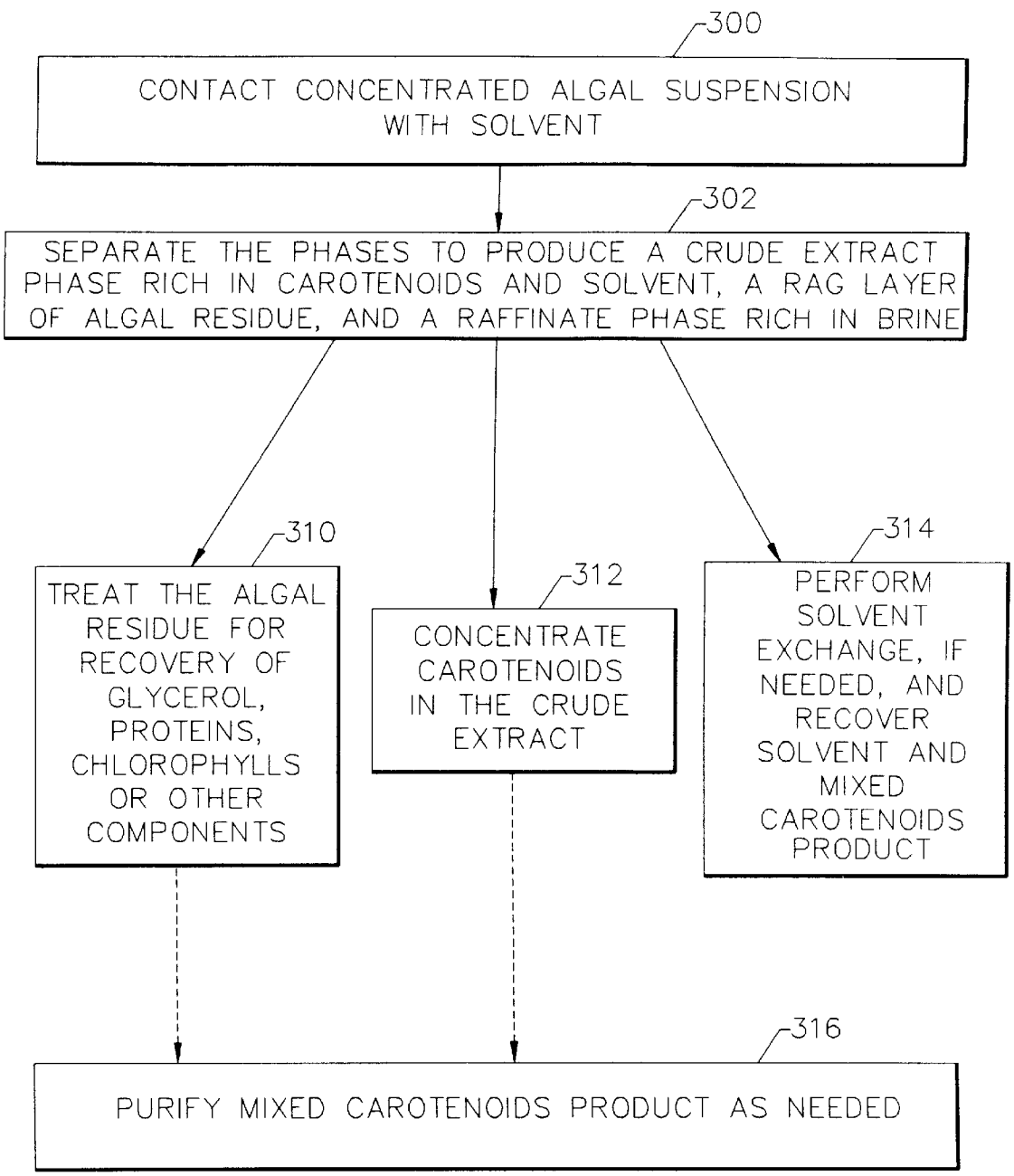
FIG. 12 is a process flow diagram for extraction of mixed carotenoids and other valuable components from algae.

A process flow diagram of typical extraction steps is shown in FIG. 12. In the initial solvent extraction step 300, the concentrated algal suspension is contacted with solvent. The carotenoids are transferred from the brine into a second fluid phase, which is the extract or solvent phase. Two phases and a rag layer typically result from the extraction process, as noted in step 302. A rag layer of algal residue is formed between the crude extract phase, which contains carotenoids and solvent, and the raffinate phase, which is rich in brine and usually contains trace amounts of carotenoids. The algal residue typically is rich in chlorophyll, glycerol, phospholipids, and proteins and can be either discarded or subjected to further processing in accordance with step 310 to recover these components.

Extraction can be performed either batchwise or continuously. A batch extraction process has proved useful. The organic and aqueous phases are sufficiently agitated so that substantially all of the carotenoids are extracted into the organic phase. Agitation is then stopped. The dispersion is allowed to settle so that three distinct regions form, the raffinate, extract, and rag layers. The layers are separated by careful decantation for further processing as outlined below.

A variety of extraction equipment can be used for continuous extraction including: single and multiple mixers and settlers; centrifugal extractors, including those manufactured by Robatel, which is located in Pittsfield, Mass. and the Podbelniak, which is manufactured by Baker Perkins of Saginaw, Mich.; and extraction columns including the Karr column, the York-Scheibel column, and the rotating disc column, all made by Glitsch Technology Corporation, which is located in Parasippany, N.Y., the Kuhni column, which is made by Kuhni in Allschwil, Switzerland, and packed and perforated plate columns.

Gravity settling is useful in a continuous extraction process. Separation of the phases can be achieved in a centrifugal or gravitational force field, but gravity settling is usually of lower cost. A coalescer may be added to assist in the decantation. The raffinate can be further coalesced to recover any additional solvent that may be entrained before being recycled to the bioreactor or returned to the pond, depending on the type of aquaculture practiced. A coalescer, liquid/liquid/solid centrifuge, flotation cell, and liquid/liquid cyclone may also be used to recover solvent from brine, or the brine may be recycled to a flotation device for cleanup.

The extraction process can be used to extract carotenoids from brine following any prior concentration step, including any of those previously mentioned, or from unprocessed brines, where the extraction is the harvesting method. In the latter case, solvent recycle from the decanter could be employed to increase the solvent to feed ratio in the mixer.

The aqueous phase can be pretreated to minimize the amount of chlorophyll extracted into the organic phase, if desired. The aqueous phase containing the biomass can be treated prior to the extraction with a base, such as NaOH, to saponify the chlorophyll and prevent it from being extracted into the organic phase with the carotenoids. Alternatively, the aqueous phase containing the biomass can be acidified to prevent chlorophyll from being extracted into the organic phase.

The solvent can be dispersed in the algal suspension prior to one or more dewatering steps. In this event, the solvent is said to be predispersed and the feed is said to be preconditioned for extraction. For example, solvent can be predispersed in the algal suspension before initiating adsorptive bubble separation.

A. Purifying and Separating the Components

The crude extract of carotenoids is separated from the rag layer and the raffinate, as noted above. The crude extract, enriched in carotenoids, and the rag layer, enriched in glycerol and protein, can each be treated for recovery of purified preparations of valuable components. Compounds that can be recovered include all-trans beta carotene, 9-cis beta carotene, alpha carotene, zeaxanthin, cryptoxanthin, lutein, glycerol, protein, and others. A variety of techniques is believed to be known to the skilled artisan for purification of crude extracts.

The crude extract can be further concentrated in accordance with step 312 by one or more of several techniques, including evaporating the solvent via a flash, distillation, wiped film evaporation, short path distillation, and molecular distillation. Proper selection of a solvent will allow this concentration step to operate at low temperatures where the carotenoids do not degrade or reisomerize. The preferred method of processing the crude extract depends on the desired product.

The carotenoids are collected as a solid phase directly from the concentration step 312 or redispersed in an edible oil through a solvent exchange, in accordance with step 314. The mixed carotenoids product is purified as needed in accordance with steps 316. An edible oil can be mixed with a flavorant prior to or after the extraction and before the evaporation so that the desired amount of flavorant is evaporated, leaving the carotenoids in the edible oil. The edible oil could be an animal oil or a mixture of vegetable oils including olive, canola, peanut, soybean, safflower, sunflower, palm, corn oil and mixtures thereof. In this manner the need for costly molecular distillation of the edible oil to produce more concentrated carotenoid suspensions can substantially be eliminated.

B. Beta carotene and Other Carotenoids

The edible oil suspension of mixed carotenoids can be sold in the human nutritional supplement, food colorant, and food fortification markets. Alternatively, products with different concentration ratios of the various carotenoids may be produced by subsequent separation steps, including those described below. The crude extract can be purified by chromatography and the resulting fractions crystallized to recover the carotenoids and the solvent. Additional unit operations can include crystallization, supercritical fluid chromatography, reverse phase chromatography, and high-performance liquid chromatography, or HPLC.

Many products can be produced from these unit operations. Supercritical fluid chromatography can separate all trans alpha carotene, cis isomers of alpha carotene, all trans beta carotene, and cis isomers of beta carotene. Reversed phase chromatography can be used to separate lutein, zeaxanthin, beta cryptoxanthin, echinenone, lycopene, alpha carotene, and beta carotene. HPLC can be used to separate beta carotene, echinenone, canthaxanthin, fucoxanthin, and astacene, 13–15 di-cis-beta carotene, 15-cis-beta carotene, beta carotene, 9-cis-beta carotene, and 13-cis-beta carotene. A combination of HPLC and supercritical fluid chromatography can be used to separate 13-13'-di-cis beta carotene, 9,13,13' tri-cis beta carotene, 9,13'-di-cis beta carotene, 15-cis beta carotene, 9,13-di-cis beta carotene, 13-cis beta carotene, 9,9'-di-cis becarotene, an all-trans beta carotene, and 9-cis beta carotene.

A high purity beta carotene extract composed of at least 40% by weight 9-cis isomer and less than 50% all-trans isomers can be prepared by separation of the isomers on an activated alumina column. An enriched 9-cis extract composed of at least 75% by weight 9-cis isomer can be prepared by crystallization of the all-trans isomer from a non-polar solvent. The high purity beta carotene extract is prepared by recovering the solvent from the crude extract and resuspending the carotenoids in a minimum amount of non-polar solvent. The solvent can be selected from ethane, hexane, heptane, octane, and petroleum ether. The non-polar extract is then passed through an activated alumina column and the fractions collected. Fractions containing the main band of orange/red carotenoid are eluted first. The fractions are collected and the solvent is evaporated under vacuum, resulting in a high purity natural beta carotene and 3% other beta carotene isomers, and 5% alpha carotene and 2% other carotenoids. The pale yellow carotenoids are eluted after the beta carotene fraction, including some beta carotene.

The column can be washed periodically to remove any polar carotenoids, lipids, and chlorophyll that are not eluted. The high purity natural 9-cis beta carotene is produced by dissolving the high purity natural beta carotene in a minimal amount of non-polar solvent warmed to 40° to 50° C. to dissolve the beta carotene, chilling the solvent to –20° C. to preferentially crystallize the all-trans isomer, and separating the solid and liquid phases. The crystallization step may be repeated to improve the purity of the crystals and the supernatant solution. The solvent is evaporated from the supernatant solution to yield a preparation enriched in 9-cis isomer to a concentration of at least 75% by weight.

C. Products and Applications

Beta carotene and other carotenoids derived by the process of the invention may be formulated for sale as any number of products. Spray dried *Dunaliella salina* powder can be incorporated into animal feeds. Products are available as suspensions of carotenoids in oil in various concentrations, microencapsulated carotenoids, and water dispersible powders of natural mixed carotenoids. Beta carotene can also be purified and sold as enriched 9 cis isomer or enriched all trans isomer. The other carotenoids obtained by the process of the invention may also be purified and sold as products.

D. Glycerol, Protein, and Other Components

The algal residue may be disposed of or further processed in accordance with step 310 to recover other valuable components from the algae such as glycerol, chlorophylls, and proteins.

The rag layer can be contacted with ethanol to recover glycerol. The ethanol can then be evaporated and the resulting glycerol residue can be purified by distillation. The glycerol may be extracted, decolorized, and distilled for sale as a useful product. The cell mass remaining after the glycerol extraction is rich in proteins and can be dried to produce a protein enriched algal meal for use in animal feeds. The cell mass can be washed with water to remove residual salts before drying.

VII. Examples

The following examples are presented to illustrate several aspects of the invention, but should not be construed to limit the invention. The examples are generally organized by the headings, depending upon the particular aspect of the invention to which the example is directed. However, it should be recognized that several aspects of the invention may be illustrated in a single example under a particular heading. The headings should not be considered exclusive of examples presented under different headings.

A. Cell Rupture in a Pump Loop

With reference to FIG. 2, the magnitude of the pressure drop and the number of passes through the pressure drop were evaluated for rupturing *Dunaliella salina* as follows. A brine containing *Dunaliella salina* was transported from a pond 34 in the Great Salt Lake to a Jameson cell 36 by a pump 38, which was a Grundfos Series C multistage centrifugal pump CR30-80LT. The brine was recirculated in a pump loop to rupture the algae. The bypass flow 46 defined the volume of recirculated flow. A bleedoff flow line 48 was used to return brine to the pond. The bypass and bleedoff flow rates were controlled by valves 50 and 52, respectively. The flow rates were varied as necessary to provide the desired percent recycle in the pump loop. The pressure drop was adjusted to the desired value using throttling valve 42.

At each discharge pressure, the total pump discharge flow rate through line 40, $Q_1$, was determined by closing valve 50 and measuring the bleedoff flow rate through line 48, $Q_4$, and the Jameson cell feed flow rate at 44, $Q_5$. The bleedoff flow rate was determined by measuring the time required to fill a 55 gallon drum. The Jameson cell feed flow rate was calculated using the following equations:

$$v = \sqrt{\frac{2\Delta p}{\rho}}$$

$$Q_5 = C_o \frac{\pi d_o^2}{4} v$$

where $v$ is the orifice velocity, $\Delta p$ is approximated by the feed pressure measured at pressure indicator 54, $\rho$ is the liquid density, $C_o$ is the orifice coefficient, which is 0.61, and $d_o$ is the orifice diameter, which is 0.3125 inches.

The total pump discharge flow rate at the specified discharge pressure can be calculated from the following mass balance. The equation applies only in the case of zero bypass flow in which valve 50 is closed.

$$Q_1 = Q_4 + Q_5$$

When valve 50 was opened to provide brine recirculation in the pump loop, the bypass flow rate was calculated from the following equation:

$$Q_2 = Q_1 - (Q_4 + Q_5)$$

where $Q_4$ and $Q_5$ were determined using the procedure described previously and $Q_2$ is the flow rate through line 46.

The percent recycle in the pump loop, R, is given by:

$$R = \frac{Q_2}{Q_5} \cdot 100\%$$

The pressure drop across throttling valve 42 ($\Delta p_t$) promotes cell rupture, and is calculated as follows:

$$\Delta p_t = p_1 - p_2$$

where $p_2$ and $p_2$ are the pressures measured at pressure indicator 56 and pressure indicator 58, respectively.

The percent of algae ruptured in the process was determined from cell count data. The number of live cells per ml was measured for the feed intake to the pump through line 60, $Q_0$, and the Jameson cell underflow stream 50, $Q_7$. The percent of algae ruptured, F, is calculated using the following equation:

$$F = \left(1 - \frac{CC_t}{CC_f}\right) \cdot 100\%$$

where, $CC_t$ and $CC_f$ are the cell counts in the feed and Jameson cell underflow samples, respectively. The cell count is defined as the number of whole cells per milliliter of brine.

B. Deep Bed Filtration

*Dunaliella salina* cells were ruptured by mixing the brine suspension in a Waring Blender for 30 seconds. One liter of brine containing a suspension of ruptured *Dunaliella salina* was filtered through a column filled with filter media. The column had an inside diameter of 30 mm and was 80 mm in length. The various filter media are shown below in Table 1.

TABLE 1

Types of filtration media used.

| Media Type | Media Size | Media Mass Uses In Test |
|---|---|---|
| Quartz sand | 0.25–0.35 mm | 43 g |
| Anthracite | 0.85–0.95 mm | 23 g |
| Glass wool | | 2.2 g |
| Mixed media | Mix of sand, anthracite & garnet | |

When the filtration was complete, the media was washed with distilled water to recover the cell mass. The water was extracted with solvent and the resulting solution was analyzed for carotenoids. The media was then washed with solvent and the resulting solution analyzed for carotenoids. The feed to the filter and filtrate were sampled and analyzed for carotenoids to determine the percent of carotenoids retained in the media. Results from seven examples are presented in Table 2.

TABLE 2

Deep bed filtration results.

| Example Number | Media Type | % Carotenoids Retained in the media | Wash Water (ml) | Carotenoids Recovered in Wash Water (mg) | Solvent Wash (ml) | Carotenoids Recovered in Solvent (mg) | Solvent |
|---|---|---|---|---|---|---|---|
| 1 | quartz | 70.4% | — | — | — | — | — |
| 2 | quartz | 72.2% | 50 | 0.94 | 30 | 0.38 | dipentene |
| 3 | anthracite | 17.9% | 100 | 0.16 | 30 | 0.02 | dipentene |
| 4 | quartz | 66.7% | 200 | 0.37 | 60 | 0.03 | dipentene |
| 5 | glass wool | 79.9% | 150 | 0.88 | 75 | 0.36 | dipentene |
| 6 | mixed media | 30.8% | — | — | — | — | dipentene |
| 7 | quartz | 83.5% | 100 | 0.82 | 24 | 0.04 | heptane |

The impact of rupturing the cells in dewatering algae by deep bed filtration is illustrated in the following example. The same procedure described in Examples 1 to 7 was used, except the cells were not ruptured prior to filtration. A deep bed of quartz sand having granules of 0.25 to 0.35 mm was used as the filtration media. The brine was conditioned before the filtration by mixing the algal suspension with TRITON X-100 nonionic surfactant in a Denver D-12 mechanical flotation cell with no air for 1 minute. Surfactant concentration was 25 ppm based on volume. Algae recovery based on carotenoid concentration was 25%.

C. Microfiltration

The apparatus for microfiltration is illustrated in FIG. 3. Algal concentrate from froth flotation cells was charged to a feed tank 62 and pumped to a cross flow microfilter 66 through a pump 64 rated at 7.5 hp, 102 amps, and 460 volts. The cross flow microfilter contained a ZrO membrane rated for 1.4 µm and having a surface area of 2.15 ft². The membrane was supplied by U.S. Filter, located in Whittier, Calif. The microfiltration unit was hexagonal in cross section with 19 channels for liquid flow. Each channel was 4 mm in diameter and 80 cm in length. A heat exchanger 68 was used to cool the feed prior to entering the filter. The pressure drop across the membrane was measured with pressure indicators 74 and 76.

The retentate 70 was returned to the feed tank for recycle to the filter. The permeate 69 was discarded. The mass of the permeate was recorded as a function of time. The flux, N, was calculated using the following equation:

$$N = \frac{M_2 - M_1}{A(t_s - t_1)}$$

where A is the cross sectional area of the filter available for flow, and $M_2$ and $M_1$ are the mass of permeate at times $t_2$ and $t_1$, respectively. The feed flow rate was measured by a flow meter 78. The temperature was measured by a thermometer. Samples were taken of the retentate and permeate, and analyzed for carotenoids.

The suspension was filtered continuously for 6 hours. Approximately 150 lbs. of permeate were removed. The flux versus time curve is shown in FIG. 4. After the initial drop in flux typically observed in cross flow microfilters, the flux remained relatively constant at 115 kg/hr/m² with no significant increase in pressure drop over the course of the run. This result was surprising, considering that the gelatinous nature of the ruptured algae would be expected to rapidly foul the membrane. It is even more surprising that carotenoids could not be detected in the permeate. Significant carotenoid losses in the permeate were expected due to the small size, less than 0.1 µm, of the carotenoid globules.

Diafiltrations were performed to reduce the salt concentration in the retentate. Fresh water was added to feed tank 62. Additional filtration and water dilution stages were performed as required to achieve the desired salt concentration in the final retentate. At the end of the 6 hour run, the remaining retentate was diluted with an equal volume of fresh water and filtered for 13 minutes to return to the initial volume. A second diafiltration was performed by addition of another equal volume of fresh water followed by filtration for 13 minutes to return to the initial volume. The flux measured for these diafiltration experiments is presented in FIG. 4.

D. Froth Flotation

1. Mechanical Froth Flotation

Brine containing a suspension of *Dunaliella salina* was charged to a Denver D-12 bench scale froth flotation machine. This froth flotation machine is designed to aspirate the proper amount of air for a given impeller speed. An 8 blade impeller with a diameter of 2.75 inches was used. A 2000 g mixing vessel was used for all of the Examples except for Example 20, where a 4000 g vessel was used. Samples were removed from the liquid over time to determine flotation kinetics and recovery of carotenoids from the brine. The concentrated froth was collected at the end of each run and analyzed for carotenoids by UV-VIS spectroscopy at 456 nm.

Experimental variables included impeller speed, gas flow rate, cell volume, initial carotenoid concentration in the brine, and surfactant dosage. Gas flow rate was varied by addition of compressed gas through the agitator shaft. Recovery data were measured for unruptured algae, ruptured algae, and for concentrated froth from previous flotations.

EXAMPLES 8 to 10

*Dunaliella salina* cells were ruptured by mixing for 30 seconds in a Waring blender. 2000 ml of brine containing a suspension of ruptured cells were charged to the flotation cell and mixed for 10 to 20 minutes. Carotenoid recoveries after 10 minutes are summarized in Table 3.

TABLE 3

Effect of impeller speed on the recovery of carotenoids for ruptured algae after 10 minutes.

| Example number | Impeller speed (rpm) | Carotenoid recovery (%) |
|---|---|---|
| 8 | 1300 | 86 |
| 9 | 1500 | 87 |
| 10 | 1700 | 86 |

EXAMPLES 11 to 16

2000 ml of brine containing a suspension of *Dunaliella salina* were charged to the flotation cell and mixed for 35 minutes. Caroenoid recoveries after 10 minutes are summarized in Table 4.

TABLE 4

Effect of impeller speed on the recovery of carotenoids from unruptured algae after ten minutes.

| Example Number | Impeller Speed (rpm) | Carotenoid recovery (%) |
|---|---|---|
| 11 | 1300 | 51 |
| 12 | 1500 | 70 |
| 13 | 1700 | 79 |
| 14 | 1700 | 72 |
| 15 | 2000 | 96 |
| 16 | 2300 | 99 |

EXAMPLES 17 to 20

Brine containing a suspension of *Dunaliella salina* was charged to the flotation cell and mixed at 1500 rpm for 35 minutes. The effect of cell volume on cartenoid recovery is summarized in Table 5.

TABLE 5

Effect of cell volume on the recovery of carotenoids from *Dunaliella salina* after 10 minutes.

| Example number | Cell volume (ml) | Carotenoid recovery (%) |
|---|---|---|
| 17 | 2000 | 79 |
| 18 | 2400 | 69 |
| 19 | 2800 | 69 |
| 20 | 4000 | 68 |

EXAMPLES 21 to 25

2000 ml of brine containing a suspension of *Dunaliella salina* were charged to the flotation cell and mixed for 10 minutes. The effect of gas flow rate on carotenoid recovery after 10 minutes is summarized in Table 6.

TABLE 6

Effect of gas flowrate and impeller speed on carotenoid recovery from unruptured *Dunaliella salina*.

| Example number | Gas flow rate | Impeller speed (rpm) | Carotenoid recovery (%) |
|---|---|---|---|
| 21 | 43 CFH | 2550 | 98 |
| 22 | 50 CFH | 2000 | 92 |
| 23 | 40 CFH | 2000 | 94 |

TABLE 6-continued

Effect of gas flowrate and impeller speed on carotenoid recovery from unruptured *Dunaliella salina*.

| Example number | Gas flow rate | Impeller speed (rpm) | Carotenoid recovery (%) |
|---|---|---|---|
| 24 | 30 CFH | 2000 | 92 |
| 25 | 40 CFH | 1500 | 84 |

EXAMPLES 26, 27, and 28

2000 ml of brine containing low, medium, and high concentrations of *Dunaliella salina* were charged to the flotation cell and mixed for 10 minutes. The effect of cell concentration on carotenoid recovery is summarized in Table 7.

TABLE 7

The effect of carotenoid concentration on carotenoid recovery after 10 minutes.

| Example number | Carotenoid concentration | Carotenoid recovery (%) |
|---|---|---|
| 26 | 0.00032 mg/ml brine (~1800 cells/ml) | 90% |
| 27 | 0.0012 mg/ml brine | 70% |
| 28 | 0.125 mg/ml brine (~1.3M cells/ml) | 66% |

EXAMPLES 29 and 30

2000 ml of brine containing a suspension of *Dunaliella salina* were charged to the flotation cell. Triton X-100 was added to the brine and the solution was mixed for one minute at 1500 rpm without air. The air valve was then opened and the suspension mixed with air for 20 minutes. Carotenoid recovery was measured after 10 minutes, and the results are summarized in Table 8.

TABLE 8

The effect of surfactant concentration on carotenoid recovery after 10 minutes.

| Example number | Surfactant conc. (ppm) | Carotenoid recovery (%) |
|---|---|---|
| 29 | 25 | 10% |
| 30 | 100 | 25% |

EXAMPLES 31 and 32

2000 ml of concentrated froth from the flotation cell were charged to the cell and mixed for 35 minutes. Carotenoid recoveries were measured after 10 minutes and are summarized in Table 9.

TABLE 9

Effect of impeller speed on carotenoid recovery from concentrated froth from previous flotations after 10 minutes.

| Example number | Impeller speed (rpm) | Carotenoid recovery (%) |
|---|---|---|
| 31 | 1500 | 94% |
| 32 | 2000 | 85% |

EXAMPLE 33

A Denver DR-8 4-cell mechanical flotation machine was fitted with an 8 flat-blade Rushtor turbine impeller in each cell in a rotor and stator arrangement. The unit was continuously fed 7 gpm of an algal suspension. The ratio of tank diameter to impeller diameter was 2.1. The ratio of tank height to tank diameter was 0.84. The ratio of rotor submergence liquid was 0.75. The impeller tip speed was held constant at 1790 ft/min for all 4 impellers. The liquid residence time was 11 minutes. The $J_g$ was 4.0 cm/s. The gas to feed ratio was 16.4. The solids fraction in the froth on a gas free basis was 0.02%. Carotenoid recovery was 78%.

2. Pneumatic Froth Flotation a. The Jameson Cell

EXAMPLE 34

Brine containing a suspension of *Dunaliella salina* was processed in a mechanical pretreatment device to rupture the cells and then treated in a Jameson cell. The Jameson cell had a ratio of downcomer diameter to orifice diameter of 8.6 and a ratio of riser diameter to downcomer diameter of 5. The cell $J_g$ was 0.44 cm/s. The jet velocity was 21.5 m/s. The downcomer superficial velocity was 0.20 m/s. The downcomer residence time was 15.1 s. The air to feed ratio was 0.52. Carotenoid recovery over the course of the run averaged 58.8%. The solids fraction in the froth was 0.02% on a gas free basis.

EXAMPLE 35

Froth generated during the run described in Example 34 was collected and processed in the Jameson cell having the geometry described in Example 34 to further concentrate the carotenoids. The cell $J_g$ was 0.27 cm/s. The jet velocity was 10.6 m/s. The downcomer superficial velocity was 0.13 m/s. The downcomer residence time was 23.2 s. The air to feed ratio was 0.49. Carotenoid recovery over the course of the run averaged 89.7%. The solids fraction in the froth was 0.5% on a gas free basis.

EXAMPLE 36

Brine containing a suspension of *Dunaliella salina* was processed in a Jameson cell having the geometry described in Example 34 without any mechanical or chemical pretreatment. The cell $J_g$ was 0.65 cm/s. The jet velocity was 46.1 m/s. The downcomer superficial velocity was 0.175 m/s. The downcomer residence time was 17.5 s. The air to feed ratio was 0.88. Carotenoid recovery over the course of the run averaged 52.8%. The solids fraction in the froth was 0.02% on a gas free basis.

EXAMPLE 37

Froth generated during the run described in Example 34 was collected and processed in a Jameson cell having the geometry described in Example 34 to further concentrate the carotenoids. The cell $J_g$ was 0.29 cm/s. The jet velocity was 11.9 m/s. The downcomer superficial velocity was 0.14 m/s. The downcomer residence time was 21.7 s. The feed pressure was 22 psi. The air to feed ratio was 0.49. Carotenoid recovery over the course of the run averaged 68%. The fraction of solids in the froth was 8.3% on a gas free basis.

EXAMPLE 38

Brine containing a suspension of *Dunaliella salina* was processed in a froth flotation device. The froth was subsequently collapsed and fed continuously to a Jameson cell having the geometry described in Example 34 at the rate of 65 liters/min. The gas rate to the cell was 1.1 SCFM. Carotenoid recovery in the froth averaged 89.7% over the course of the one hour run.

EXAMPLE 39

Brine containing a suspension of *Dunaliella salina* was processed in a froth flotation device. The underflow stream was collected and fed continuously to a Jameson cell having the geometry described in Example 34 at the rate of 62 liters/min. The gas rate to the cell was 1.7 SCFM. Carotenoid recovery in the froth averaged 79%.

b. Multistage Loop Flow Froth Flotation Column (MSTLFLO)

A MSTLFLQ column was used for Examples 40 to 47 below that was 4 inches in diameter, 125 inches tall, and fitted with three draft tubes. The draft tube aspect ratio was 12.2. The ratio of draft tube diameter to column diameter was 2. The launder diameter to column diameter ratio was 2. No frother was added. The pH of the brine ranged between 6 and 7. A sintered metal sparger was used to sparge air into the column. The sparger was 1 inch in diameter, 6 inches long, and had a pore size of 10 microns. The sparger was located in the bottom of the lowest draft tube. The feed distributor was located 6 inches above the top draft tube.

EXAMPLE 40

The MSTLFLO column was filled with brine containing carotenoids. The flow of air and feed commenced at the rates of 1.5 SCFH and 3.4 liters/min, respectively, to give an air to feed ratio of 0.21. The column was operated in a continuous mode, and samples of the feed, froth, and underflow were collected at 5 minute intervals. The $J_g$ was 0.15 cm/s and the liquid residence time was 5.2 minutes. The solids fraction in the froth on a gas free basis was about 6%. The recovery of carotenoids was 78%.

EXAMPLE 41

The MSTLFLO column was filled with brine containing carotenoids. The flow of air and feed commenced at the rates of 1.5 SCFH and 6 liter/min, respectively, to give an air to feed ratio of 0.12. The column was operated in a continuous mode, and samples of the feed, froth and underflow were collected at 5 minute intervals. The $J_g$ was 0.15 cm/s and the liquid residence time was 3.2 minutes. The solids fraction in the froth on a gas free basis was about 17%. The recovery of carotenoids was 76%.

EXAMPLE 42

The MSTLFLO column was first filled with brine containing carotenoids. The flow of air commenced at the rate of 3 SCFH. The column was operated in batch mode. Samples of the feed, froth, and underflow were collected after a flotation time of 20 minutes. The $J_g$ was 0.29 cm/s. The solids fraction in the froth on a gas free basis was about 11%. The recovery of carotenoids was 83%.

EXAMPLE 43

The MSTLFLO column as in Example 41 was charged with brine containing *Dunaliella salina* that was previously processed in a flotation device. The gas rate to the column varied from 3 to 4 SCFH. The recovery of carotenoids in the froth was more than 87% after 25 minutes.

EXAMPLE 44

Brine containing a suspension of *Dunaliella salina* was processed in a flotation device. The froth was subsequently collapsed and fed continuously to the top of the MSTLFLO column as in Example 41 at the rate of 2 liters/min. Air was sparged at the base of the column at the rate of 2 SCFH. The column was operated continuously for over 30 minutes. The average carotenoid recovery in the froth was 81.5%.

EXAMPLE 45

In a run similar to Example 41, brine was fed to the MSTLFLO column at the rate of 3.25 liters/min. Carotenoid recovery in the froth averaged 86.3% over the course of the 30 minute run.

EXAMPLE 46

In a run similar to Example 45, brine was Led to the MSTLFLO column at the rate of 1.14 liters/min. Carotenoid recovery in the froth averaged 84.9% over the course of the 35 minute run.

EXAMPLE 47

In a run similar to Example 41, brine was fed to the MSTLFLO column at the rate of 0.69 liters/min. Carotenoid recovery in the froth averaged 81.1% over the course of the 45 minute run.

c. Canadian Column

The MSTLFLO column described above was operated with all the draft tubes removed. No frother was added. The pH of the brine ranged between 6 and 7. The same sparger was used. The feed distributor was located about 36 inches below the froth overflow weir.

EXAMPLE 48

The bubble column was filled with brine containing carotenoids. The flow of air and feed commenced at the rates of 5 SCFH and 5.8 liters/min, respectively, to give an air to feed ratio of 0.41. The column was operated in a continuous mode. Samples of the feed, froth, and underflow were collected at 5 minute intervals. The $J_g$ was 0.49 cm/s. The liquid residence time was 3.1 minutes. The solids loading in the froth on a gas free basis was about 0.7%. The recovery of carotenoids was 65%.

EXAMPLE 49

Brine containing a suspension of *Dunaliella salina* was processed in a flotation device. The froth was subsequently collapsed and charged to the 4-inch diameter bubble column. Air was added at a rate of 20 SCFH at the base of the column via the sparger. The recovery of carotenoids in the froth was 90% after 12 minutes flotation time.

d. Air Sparged Hydrocyclone (ASH)

EXAMPLE 50

The flow of gas to the air sparged hydrocyclone was started at the desired rate before the feed flow commenced at the setpoint value. The ASH unit consisted of a plastic shell that contained a 2 inch diameter polyethylene membrane approximately 18 inches in length with an average pore size of 20 microns. The gas pressure on the pressurized side of the membrane was maintained between 15 and 10 psig. No surface active materials were added to facilitate the flotation. Samples were taken of the feed, froth, and underflow to quantitate ASH performance. The $J_g$ was 5.9 cm/s. The gas to feed ratio was held at 5.8. The liquid residence time was 1.3 s. The solids fraction in the froth was 0.09% on a gas free basis. The recovery of carotenoids was 68%.

EXAMPLES 51 to 54

The ASH unit of Example 50 was evaluated to determine carotenoid recovery and concentration factor with ruptured algae. The results are summarized below in Table 10. Compressed air was introduced through the porous walls of the cyclone. The feed material was charged to the top of the cyclone. The carotenoid enriched froth exited the overflow while the brine depleted in algae exited the underflow.

TABLE 10

ASH carotenoid recovery and concentration.

| Example number | Feed Pressure (psig) | Feed Flowrate (gpm) | Gas/Feed Volume Ratio, Q* | Carotenoid Recovery (%) |
|---|---|---|---|---|
| 51 | 7 | 11.8 | 5.7 | 40 |
| 52 | 6 | 11.8 | 2.9 | 52 |
| 53 | 7 | 11.8 | 5.7 | 49 |
| 54 | 7 | 11.8 | 5.8 | 68 |

E. Recovery of Valuable Components

1. Solvent Distribution Coefficients

Distribution coefficients for carotenoids from *Dunaliella salina* between brine and various solvents were measured at 25° C. to identify suitable solvents for the extraction operation. Three ml of solvent and 12 ml of algal concentrate were charged to a 25 ml test tube. These tubes were mixed for a time sufficient for complete mass transfer prior to decantation and sampling. The results are summarized in Table 11, and the distribution coefficient is defined as the carotenoid concentration in the organic phase divided by its concentration in the aqueous phase.

TABLE 11

Distribution coefficients of carotenoids between brine and several organic solvents at 25° C.

| Example Number | Solvent | Carotenoids recovery in the solvent (%) | Distribution coefficient (organic/aqueous) |
|---|---|---|---|
| 55 | Benzaldehyde | 99.4 | 159 |
| 56 | Decyl alcohol | 98.6 | 73 |
| 57 | Ethyl Acetate | 100 | >1000 |
| 58 | Ethyl butyrate | 98.7 | 79 |
| 59 | 2-Heptanone | 99.7 | 31 |
| 60 | cis-3-Hexene-1-ol | 99.7 | 31 |
| 61 | Isoamyl Acetate | 99.9 | 958 |
| 62 | Isobutyl Acetate | 100 | >1000 |
| 63 | Octyl Aldehyde | 93.2 | 14 |

2. Liquid extraction

Brine containing a suspension of *Dunaliella salina* was charged to a flotation cell and mixed for 10 minutes. The concentrated froth was collected and mixed with air in the flotation cell for 10 minutes. 2000 ml of the twice concentrated froth containing carotenoids and 400 ml of solvent were charged to a 3 liter mixer with the geometry given in Table 12 below.

TABLE 12

Dimensions cf the mixing vessel and impeller used for the extraction mass-transfer kinetics test.

| Item | Dimension |
|---|---|
| Impeller diameter | 6-flat-blade Rushton turbine<br>2.5 inches |
| disc diameter | 2.0 inches |
| vane width | 0.5 inches |
| vane height | 9/16 inch |

TABLE 12-continued

Dimensions cf the mixing vessel and impeller used for the extraction mass-transfer kinetics test.

| Item | Dimension |
|---|---|
| Vessel diameter | cylindrical with 4 equally-spaced baffles<br>5.75 inches |
| liquid height | 7.75 inches |

The mixture was agitated at 600 tpm for 20 minutes. Samples of brine were periodically removed to determine mass-transfer kinetics. After 20 minutes, the mixer was stopped and the phase separation time was recorded. The oil phase was decanted, and the brine phase returned to the mixer. Four hundred milliliters of fresh solvent were charged to the extractor, and the multiphase mixture was agitated at 600 rpm for 20 minutes. The phases were again allowed to separate for 20 minutes. The solvent phases from both extraction stages were allowed to settle for an additional four hours to reduce the volume of the gelatinous algal residue. The solid phase was then centrifuged to separate the solvent and brine phases from the algal residue. The solvent was evaporated from the carotenoid extract and olive oil was added to produce a suspension of carotenoids in olive oil. Extraction and phase separation data are provided in the following examples.

EXAMPLE 65

Extraction of carotenoids from concentrated froth into heptane.

The general extraction procedure described above was followed. 2530 g of concentrated froth and 280 g of heptane were charged to the mixer. Recovery data are summarized in Table 13.

TABLE 13

Mixer/settler kinetics for the extraction of carotenoids from *Dunaliella salina* with heptane.

| Stage # | Mixing time (min) | Carotenoid recovery (%) |
|---|---|---|
| 1 | 20 | 97.7% |
| 2 | 20 | 71.7% |

EXAMPLE 66

Extraction of carotenoids from concentrated froth into limonene.

The general extraction procedure described above was followed. A mixer was charged with 2516 g of concentrated froth and 343 g of limonene. Recovery data are presented in Table 14.

TABLE 14

Mixer/settler kinetics for the extraction of carotenoids from *Dunaliella salina* with limonene.

| Stage # | Mixing time (min) | Carotenoid recovery (%) |
|---|---|---|
| 1 | 20 | 95.0% |
| 2 | 20 | 84.7% |

EXAMPLE 67

Extraction of carotenoids from concentrated froth into ethyl butyrate.

The general extraction procedure described above was followed. The mixer was charged with 2499 g of concentrated froth and 353 g of ethyl butyrate. Recovery data are presented are presented in Table 15. The impeller speed was 800 rpm.

TABLE 15

Mixer settler kinetics for the extraction of carotenoids from Dunaliella salina with ethyl butyrate.

| Stage # | Mixing time (min) | Carotenoid recovery (%) |
|---|---|---|
| 1 | 10 | 95.4% |

EXAMPLE 68

Extraction of carotenoids from concentrated froth into olive oil.

The general extraction procedure described above was followed. The mixer was charged with 1845 g of concentrated froth and 280 g of olive oil. Carotenoid recovery was 77% after 10 minutes.

EXAMPLE 69

Raffinate cleanup.

A flotation cell was charged with 2000 ml of raffinate from the second stage extraction, which was mixed for 20 minutes at 2000 rpm. Carotenoid recovery in the froth after 16 minutes was 82%.

EXAMPLE 70

Raffinate cleanup.

Saturated NaCl brine was contacted with solvent and the mixture was allowed to reach equilibrium at 25° C. The solvent concentration in the saturated brine was measured. Activated carbon was added to the solution and the slurry mixed until equilibrium was reached. The carbon was allowed to settle from the slurry and the brine sampled to determine solvent concentration. Results are provided in Table 16.

TABLE 16

Solvent concentration in saturated NaCl brine before and after carbon bed adsorption. The detection limit of solvent in brine is 5 ppb.

| Solvent | Concentration of solvent in saturated NaCl brine before carbon bed adsorption | Concentration of solvent in saturated NaCl brine after carbon bed adsorption |
|---|---|---|
| heptane | 875 ppb | <5 ppb |
| limonene | 125 ppb | <5 ppb |

3. Liquid Extraction Mass Transfer Kinetics

Mass-transfer kinetics were experimentally measured in the 3-liter cylindrical vessel with the geometry summarized in Table 12. The impeller was centrally located in the vessel. Samples of the liquid/liquid dispersion were collected as a function of time, and the carotenoid concentration in the aqueous phase was measured. Results of this study are summarized in Table 17.

TABLE 17

Effect of impeller speed and solvent to feed ratio on the carotenoid recovery from liquid extraction.

| Example number | Solvent | Impeller speed (rpm) | Solvent/Feed ratio (v/v) | Carotenoid recovery after 10 minutes (%) |
|---|---|---|---|---|
| 71 | Limonene | 600 | 0.20 | 92.1 |
| 72 | Limonene | 600 | 0.15 | 91.6 |
| 73 | Limonene | 600 | 0.10 | 87.8 |
| 74 | Limonene | 600 | 0.05 | 82.3 |
| 75 | Ethyl Butyrate | 600 | 0.20 | 99.1 |
| 76 | Ethyl Butyrate | 600 | 0.15 | 97.8 |
| 77 | Ethyl Butyrate | 600 | 0.10 | 97.8 |
| 78 | Ethyl Butyrate | 600 | 0.05 | 97.1 |
| 79 | Ethyl Butyrate | 500 | 0.10 | 96.9 |
| 80 | Ethyl Butyrate | 700 | 0.10 | 98.5 |

4. Continuous Extraction of Carotenoids With Limonene

EXAMPLE 81

Brine containing a suspension of Dunaliella salina was fed at 10 gpm to a Denver #5 Water Treatment Flotation Cell with gallonse of approximately 100 gallons. Concentrated froth was recovered from the flotation cell and fed to the 3-liter mixer along with limonene. The geometry of the mixer and impeller were identical to those listed in Table 12, and the impeller speed was 600 rpm. Effluent from the mixer was pumped into a decanter through an in line strainer to break up the gelatinous algal residue. The decanter was fitted with a four-inch diameter by 12 inch long coalescer pad from Otto York in Parasippany, N.Y. The solvent phase overflowed the decanter into a surge tank from which it was pumped into the flash pot. Olive oil was added to the flash pot prior to operation of the unit. Solvent was evaporated from the flash pot and the carotenoids recovered as a suspension in olive oil. The evaporated solvent was condensed and recycled to the mixer. Recovery from the extraction is given in Table 18. Recovery from the froth flotation cell averaged 60% over the course of the run.

TABLE 18

Extraction efficiency for continuous extraction of carotenoids from brine with limonene.

| Volume fraction of the dispersed phase (limonene) | Carotenoid recovery (%) |
|---|---|
| 0.2 | 83.2 |
| 0.15 | 81.2 |

The above invention has been described with respect to particular preferred embodiments. However, the foregoing description is not intended to limit the invention to the illustrated embodiments, and the skilled artisan should recognize that variations can be made within the spirit and scope of the invention as described in the foregoing specification. The invention includes all alternatives, modifications, and equivalents that may be included within the spirit and scope of the invention as defined by the appended claims.

What is claimed is:

1. A process for dewatering an aqueous suspension of microalgae comprising the steps of:
   (a) obtaining an aqueous suspension of algae from a source thereof;

(b) rupturing the algal cells;

(c) introducing the aqueous suspension into a froth flotation column selected from the group consisting of a Jameson cell and a multi-stage loop flow froth floatation column for downward gravity flow therein;

(d) generating fine bubbles of a gas for establishing a net countercurrent flow through the aqueous suspension in intimate contact with the aqueous suspension;

(e) adsorbing algal cells onto the bubbles to form bubble and alga agglomerates; and (f) forming a froth of bubble and alga agglomerates.

2. The process of claim 1 wherein the step (d) of generating fine bubbles of a gas comprises sparging gas into the column.

3. The process of claim 1 wherein the step (d) of generating fine bubbles of a gas is accomplished externally of the column and the bubbles are introduced into the column.

4. The process of claim 1 further comprising the step of circulating the aqueous suspension in loop-flow within the column to promote intimate contact of fine bubbles and algal cells.

5. The process of claim 1 wherein the column includes at least one loop-flow zone defined by a vertically oriented baffle that divides the column into a riser and a downcomer wherein the gas and liquid are in cocurrent upflow in the riser and cocurrent downflow in the downcomer to promote intimate contact.

6. The process of claim 5 wherein the column includes multiple loop-flow zones, each separated from the other by a baffle zone.

7. The process claim 6 further comprising in a baffle zone above the loop-flow zone the steps of 1) diverting gas flow upwardly, thereby minimizing gas bypass into the downcomer region, and 2) diverting liquid flow downwardly and into the downcomer region, whereby liquid communication between adjacent loop flow zones is substantially eliminated.

8. The process of claim 5 wherein the vertical baffle consists of a draft tube concentrically mounted in the column.

9. The process of claim 1 wherein the column includes at least one loop-flow zone defining a radially inward region and a radially outward annular region, the process further comprising the step of promoting a higher gas holdup in the radially inward region than in the annular region, whereby the algal suspension is circulated in a loop-flow upwardly through the radially inward region and downwardly through the annular region to promote intimate contact.

10. The process of claim 9 wherein the column includes multiple loop-flow zones, each separated from the other by a baffle zone.

11. The process claim 10 further comprising in a baffle zone above the loop-flow zone the steps of 1) diverting gas flow upwardly, thereby minimizing gas bypass into the downcomer region, and 2) diverting liquid flow downwardly and into the downcomer region, whereby liquid communication between adjacent loop flow zones is substantially eliminated.

12. The process of claim 9 wherein the vertical baffle consists of a draft tube concentrically mounted in the column.

13. The process of claim 1 wherein the column includes at least one loop-flow zone defining a radially inward region and a radially outward annular region, the process further comprising the step of promoting a higher gas holdup in the radially outward annular region than in the radially inward region, whereby the algal suspension is circulated in a loop-flow downwardly through the radially outward annular region and upwardly through the radially inward region to promote intimate contact.

14. The process of claim 13 wherein the column includes multiple loop-flow zones, each separated from the other by a baffle zone.

15. The process claim 14 further comprising in a baffle zone above the loop-flow zone the steps of 1) diverting gas flow upwardly, thereby minimizing gas bypass into the downcomer region, and 2) diverting liquid flow downwardly and into the downcomer region, whereby liquid communication between adjacent loop flow zones is substantially eliminated.

16. The process of claim 13 wherein the vertical baffle consists of a draft tube concentrically mounted in the column.

17. The process of claim 1 further comprising the step of collapsing the froth and wherein steps (c) through (f) are repeated to further concentrate the aqueous suspension.

18. The process of claim 1 wherein the aqueous suspension is of the alga *Dunaliella salina* in brine.

19. A process for dewatering the algal *Dunaliella salina* in brine comprising the steps of:

(a) obtaining an aqueous suspension of algae from a source thereof;

(b) rupturing the algal cells;

(c) introducing the aqueous suspension into a froth flotation column selected from the group consisting of a Jameson cell and a multi-stage loop flow froth floatation column for downward gravity flow therein;

(d) generating fine bubbles of a gas for establishing a net countercurrent flow through the aqueous suspension in intimate contact with the aqueous suspension;

(e) circulating the suspension in a loop-flow within the column to promote intimate contact of fine bubbles and algal cells;

(f) adsorbing algal cells onto the bubbles to form bubble and alga agglomerates; and (g) forming a froth of bubble and alga agglomerates.

20. The process of claim 19 wherein the column includes at least one loop-flow zone defined by a vertically oriented baffle that divides the column into a riser and a downcomer wherein the gas and liquid are in cocurrent upflow in the riser and cocurrent downflow in the downcomer to promote intimate contact.

21. The process of claim 20 wherein the column includes multiple loop-flow zones, each separated from the other by a baffle zone.

22. The process claim 21 further comprising in a baffle zone above the loop-flow zone the steps of 1) diverting gas flow upwardly, thereby minimizing gas bypass into the downcomer region, and 2) diverting liquid flow downwardly and into the downcomer region, whereby liquid communication between adjacent loop flow zones is substantially eliminated.

23. The process of claim 20 wherein the vertical baffle consists of a draft tube concentrically mounted in the column.

24. A process for separating the alga *Dunaliella salina* from brine for the subsequent recovery of mixed carotenoids from the alga, the process comprising the steps of:

a) obtaining a suspension of *D. salina* in brine from a source thereof;

b) rupturing the algal cells;

c) introducing the brine into a multi-stage loop-flow flotation column for net downward gravity flow therein, the column including at least two loop-flow zones defined by a vertical baffle to divide the column into a riser and a downcomer, wherein the gas and brine are in cocurrent upward flow in the riser and cocurrent downward flow in the downcomer;

d) dispersing the gas into fine bubbles by sparging the gas into the riser of the lowermost loop-flow zone for countercurrent flow through the brine;

e) promoting a higher gas holdup in the riser than in the downcomer, thereby circulating the brine in loop-flow upwardly through the riser and downwardly through the downcomer;

f) diverting gas flow from the riser upwardly, thereby minimizing gas bypass into the downcomer;

g) diverting liquid flow from the riser downwardly into downcomer, whereby liquid communication between adjacent loop flow zones is substantially eliminated, whereby the fine bubbles and algal cells are intimately contacted to adsorb the algae onto the surfaces of the bubbles; and h) generating a froth enriched in algae, whereby the algae are separated from the brine.

25. The process of claim 24 further comprising the step of collapsing the froth to obtain an algal concentrate and wherein the steps (c) through (i) are repeated to provide an extractable concentration of mixed carotenoids.

26. The process of claim 24 further comprising the step of collapsing the froth to obtain an algal concentrate and wherein the steps (c) through (i) are repeated to provide a concentration of mixed carotenoids suitable for cross flow micro-filtration.

27. The process of claim 24 further comprising the steps of a) cross-flow micro-filtering the algal concentrate to provide a concentration of the mixed carotenoids in the retentate suitable for dense gas extraction, and b) extracting the mixed carotenoids from the retentate by dense gas extraction to provide a dry extract of mixed carotenoids.

28. The process of claim 27 further comprising the step of purifying the mixed carotenoids by chromatography.

29. The process of claim 24 wherein the superficial gas velocity, $J_g$, is from about 0.1 to 1.0 cm/s.

30. The process of claim 24 wherein the gas to feed ratio is from about 0.1 to 1.5.

31. The process of claim 24 wherein the liquid residence time is from about 2 to 20 minutes.

32. The process of claim 24 wherein the solids fraction in the froth on a gas free basis is from about 60 ppm to 17 percent by weight of the gas-free froth.

33. The process of claim 24 wherein the gas does not contain oxygen.

34. A process for extracting mixed carotenoids from the alga *Dunaliella salina*, the process comprising the steps of:

a) obtaining a suspension of *D. salina* in brine from a source thereof;

b) rupturing the algal cells;

c) introducing a feed of the algal suspension into a multi-stage loop-flow flotation column for net downward gravity flow therein, the column including at least two loop-flow zones, each defining a radially inward region and a radially outward annular region;

d) sparging a gas in the absence of oxygen into the radially inward region of the lowermost loop-flow zone for net countercurrent flow through the algal suspension at a superficial gas velocity, $J_g$, of from about 0.1 to 1.0 cm/s and at a gas to feed ratio of from about 0.1 to 1.5;

e) promoting a higher gas holdup in the radially inward region than in the annular region, thereby circulating the algal suspension in a loop-flow upwardly through the radially inward region and downwardly through the annular region;

f) diverting gas flow from the radially inward region upwardly and radially inwardly, thereby minimizing gas bypass into the annular region;

g) diverting liquid flow downwardly and radially outwardly into the annular region, whereby backmixing is substantially eliminated, and the fine bubbles and algal suspension are intimately contacted to adsorb the algae onto the surfaces of the bubbles;

h) generating a froth enriched in algae, whereby the algae are separated from the brine;

i) collapsing the froth to obtain an algal concentrate; and j) repeating steps c) through i) to provide a concentration of mixed carotenoids having a solids fraction in the froth on a gas-free basis of from about 1 to 17 percent by weight of the gas-free froth.

* * * * *